(12) United States Patent
Watanabe et al.

(10) Patent No.: US 8,426,110 B2
(45) Date of Patent: Apr. 23, 2013

(54) CHEMICALLY AMPLIFIED POSITIVE RESIST COMPOSITION, PATTERNING PROCESS, AND ACID-DECOMPOSABLE KETO ESTER COMPOUND

(75) Inventors: Takeru Watanabe, Joetsu (JP); Tomohiro Kobayashi, Joetsu (JP); Katsuya Takemura, Joetsu (JP); Jun Hatakeyama, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/362,445

(22) Filed: Jan. 31, 2012

(65) Prior Publication Data

US 2012/0196227 A1    Aug. 2, 2012

(30) Foreign Application Priority Data

Jan. 31, 2011   (JP) .................... 2011-017812

(51) Int. Cl.
*G03F 7/004* (2006.01)
*C07C 69/608* (2006.01)

(52) U.S. Cl.
USPC ........ 430/270.1; 430/326; 430/905; 430/910; 562/116; 562/126

(58) Field of Classification Search ............... 430/270.1, 430/326, 905, 910; 560/116, 126
See application file for complete search history.

(56) References Cited

U.S. PATENT DOCUMENTS

| | | | |
|---|---|---|---|
| 5,100,917 A * | 3/1992 | Flynn et al. .................... 514/510 |
| 5,158,855 A * | 10/1992 | Sugiyama et al. ............. 430/192 |
| 5,580,694 A * | 12/1996 | Allen et al. .................. 430/270.1 |
| 6,132,936 A * | 10/2000 | Jung ........................... 430/281.1 |
| 6,258,508 B1 * | 7/2001 | Kim et al. .................... 430/270.1 |
| 6,274,286 B1 | 8/2001 | Hatakeyama et al. |
| 6,448,420 B1 | 9/2002 | Kinsho et al. |
| 6,743,564 B2 | 6/2004 | Hatakeyama et al. |
| 6,749,988 B2 | 6/2004 | Hatakeyama et al. |
| 6,821,705 B2 * | 11/2004 | Nagai et al. ................. 430/270.1 |
| 6,916,593 B2 | 7/2005 | Hatakeyama et al. |
| 7,005,230 B2 * | 2/2006 | Yamamoto et al. ........ 430/270.1 |
| 7,132,218 B2 * | 11/2006 | Toishi et al. ............... 430/270.1 |
| 7,141,351 B2 | 11/2006 | Watanabe et al. |
| 7,141,352 B2 | 11/2006 | Watanabe et al. |
| 7,179,581 B2 | 2/2007 | Watanabe et al. |
| 7,252,925 B2 | 8/2007 | Watanabe et al. |
| 7,261,995 B2 | 8/2007 | Watanabe et al. |
| 7,276,324 B2 | 10/2007 | Watanabe et al. |
| 7,378,548 B2 | 5/2008 | Watanabe et al. |
| 7,468,236 B2 | 12/2008 | Watanabe et al. |
| 7,537,880 B2 | 5/2009 | Harada et al. |
| 7,622,242 B2 | 11/2009 | Hatakeyama et al. |
| 7,629,108 B2 | 12/2009 | Watanabe et al. |
| 7,771,913 B2 | 8/2010 | Kaneko et al. |
| 8,057,981 B2 | 11/2011 | Harada et al. |
| 2002/0042018 A1 * | 4/2002 | Maeda et al. .............. 430/270.1 |
| 2004/0146802 A1 * | 7/2004 | Yamamoto et al. ........ 430/270.1 |
| 2008/0090172 A1 | 4/2008 | Hatakeyama et al. |
| 2009/0208873 A1 | 8/2009 | Harada et al. |
| 2009/0274978 A1 | 11/2009 | Ohashi et al. |
| 2009/0280434 A1 | 11/2009 | Harada et al. |
| 2010/0009299 A1 | 1/2010 | Watanabe et al. |
| 2010/0112482 A1 | 5/2010 | Watanabe et al. |
| 2010/0136482 A1 | 6/2010 | Harada et al. |

FOREIGN PATENT DOCUMENTS

| | | |
|---|---|---|
| JP | 6-236033 A | 8/1994 |
| JP | 11-084639 A | 3/1999 |
| JP | 2001-166476 A | 6/2001 |
| JP | 2001-194776 A | 7/2001 |
| JP | 2001-296659 A | 10/2001 |
| JP | 2002-226470 A | 8/2002 |
| JP | 2002-249478 A | 9/2002 |
| JP | 2002-363146 A | 12/2002 |
| JP | 2002-363148 A | 12/2002 |
| JP | 2002-363152 A | 12/2002 |
| JP | 2003-012621 A | 1/2003 |
| JP | 2004-347735 A | 12/2004 |
| JP | 2004-347736 A | 12/2004 |
| JP | 2004-347738 A | 12/2004 |
| JP | 2005-132749 A | 5/2005 |
| JP | 2005-165295 A | 6/2005 |
| JP | 2005-306812 A | 11/2005 |
| JP | 2006-176468 A | 7/2006 |
| JP | 2007-108451 A | 4/2007 |
| JP | 3944669 B2 | 7/2007 |
| JP | 3988517 B2 | 10/2007 |
| JP | 2007-297590 A | 11/2007 |
| JP | 2008-107513 A | 5/2008 |
| JP | 2008-111103 A | 5/2008 |
| JP | 2008-122932 A | 5/2008 |
| JP | 2009-098638 A | 5/2009 |
| JP | 2009-191151 A | 8/2009 |
| JP | 2009-192784 A | 8/2009 |
| JP | 2009-269953 A | 11/2009 |
| JP | 2009-276363 A | 11/2009 |
| JP | 2010-107695 A | 5/2010 |
| JP | 2010-134012 A | 6/2010 |
| JP | 2010-164933 A | 7/2010 |

* cited by examiner

*Primary Examiner* — John Chu
(74) *Attorney, Agent, or Firm* — Westerman, Hattori, Daniels & Adrian, LLP

(57) ABSTRACT

A chemically amplified positive resist composition comprises an acid-decomposable keto ester compound of steroid skeleton which is insoluble in alkaline developer, but turns soluble in alkaline developer under the action of acid. The composition is exposed to EB, deep-UV or EUV and developed to form a pattern with a high resolution and improved LER.

7 Claims, No Drawings

CHEMICALLY AMPLIFIED POSITIVE RESIST COMPOSITION, PATTERNING PROCESS, AND ACID-DECOMPOSABLE KETO ESTER COMPOUND

CROSS-REFERENCE TO RELATED APPLICATION

This non-provisional application claims priority under 35 U.S.C. §119(a) on Patent Application No. 2011-017812 filed in Japan on Jan. 31, 2011, the entire contents of which are hereby incorporated by reference.

TECHNICAL FIELD

This invention relates to a radiation-sensitive chemically amplified positive resist composition. More particularly, it relates to a chemically amplified positive resist composition suited for use in the lithography of micropatterning using a variety of radiation including deep-UV, typically KrF and ArF excimer laser, EUV, x-rays such as synchrotron radiation, and charged particle beam such as electron beam; a pattern forming process using the composition; and a novel acid-decomposable keto ester compound.

BACKGROUND ART

While the recent drive for higher integration densities and operating speeds in LSI devices makes it necessary to further reduce the pattern rule, deep-UV lithography has been investigated as the advanced micropatterning technology. Among others, the KrF or ArF excimer laser lithography is developed as an essential technology for micropatterning to a feature size of 0.3 µm or less and has been utilized in a commercial scale.

With respect to chemically amplified positive resist compositions adapted for the photolithography using excimer laser light, specifically KrF excimer laser light of 253 nm wavelength or ArF excimer laser light of 193 nm wavelength as a light source, the primary requirement is, of course, a high transparency at the relevant wavelength. They are also required to meet a high etch resistance sufficient to comply with film thickness reduction, a high sensitivity sufficient to minimize the burden to expensive optical materials, and among others, a high resolution sufficient to form an accurate fine pattern. The key to fulfill these requirements is to develop a base resin featuring high transparency, high rigidity and high reactivity. Active efforts have been devoted for such development, with some fruitful results being available. Active studies are also made on ArF immersion, EUV and EB lithography. In the current situation taking further steps toward miniaturization, not only a higher resolution is required, but it is one of important tasks to reduce irregularities on pattern sidewalls, known as line edge roughness (LER).

One means for improving the resolution and LER of chemically amplified positive resist compositions used in the excimer laser photolithography is by adding an acid-decomposable low molecular weight compound. Known are acid-decomposable ester compounds having a hydroxyl or ester group and a steroid structure which are decomposed under the action of acid to increase their solubility in alkaline developer. See JP-A H06-236033, JP 3944669, and JP 3988517, for example. However, resist compositions comprising these compounds are still insufficient in improving LER, or are sometimes degraded in resolution as the feature size is further reduced. A further improvement is desired.

Citation List
Patent Document 1: JP-A H06-236033
Patent Document 2: JP 3944669 (U.S. Pat. No. 6,448,420)
Patent Document 3: JP 3988517 (U.S. Pat. No. 6,821,705)

SUMMARY OF INVENTION

In conjunction with the lithography of micropatterning using a variety of radiation including deep-UV, typically KrF and ArF excimer laser, EUV, x-rays such as synchrotron radiation, and charged particle beam such as electron beam, an object of the invention is to provide a chemically amplified positive resist composition meeting both high resolution and low LER; a pattern forming process using the composition; and a novel acid-decomposable keto ester compound used therein.

One embodiment of the invention is a chemically amplified positive resist composition comprising one or more acid-decomposable keto ester compound of steroid skeleton which is insoluble in alkaline developer, but turns soluble in alkaline developer under the action of acid, represented by the general formula (1):

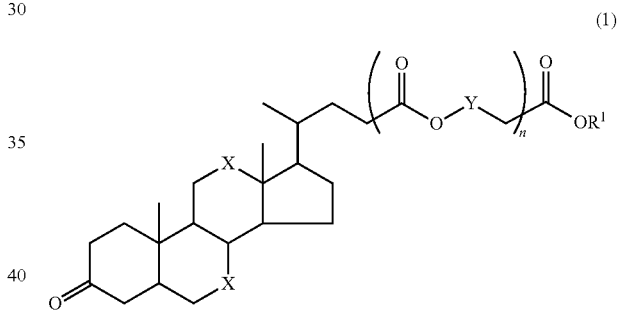

wherein $R^1$ is such an acid labile group having 6 to 20 carbon and oxygen atoms in total that $-COOR^1$ is decomposed to generate carboxyl under the action of acid, X is each independently a carbonyl group ($-CO-$) or methylene group ($-CH_2-$), Y is each independently a single bond or a $C_1$-$C_6$ alkylene group, and n is an integer of 0 to 2.

Another embodiment of the invention is a chemically amplified positive resist composition comprising (A) one or more acid-decomposable keto ester compound of steroid skeleton which is insoluble in alkaline developer, but turns soluble in alkaline developer under the action of acid, represented by the general formula (1), (B) an organic solvent, (C) a base resin having an acidic functional group protected with an acid labile group, which is substantially insoluble in alkaline developer, but turns soluble in alkaline developer when the acid labile group is decomposed, (D) an acid generator as essential components, (E) a quencher and (F) a surfactant as optional components.

In a preferred embodiment, the acid-decomposable keto ester compound has the general formula (2):

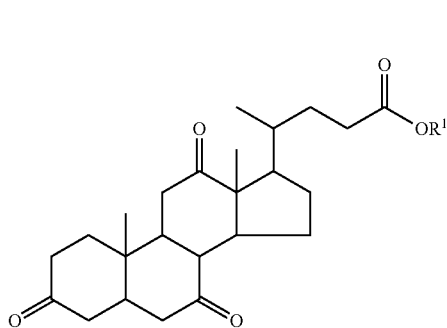

(2)

wherein $R^1$ is such an acid labile group having 6 to 20 carbon and oxygen atoms in total that —COOR$^1$ is decomposed to generate carboxyl under the action of acid.

In a more preferred embodiment, the acid-decomposable keto ester compound has the general formula (3):

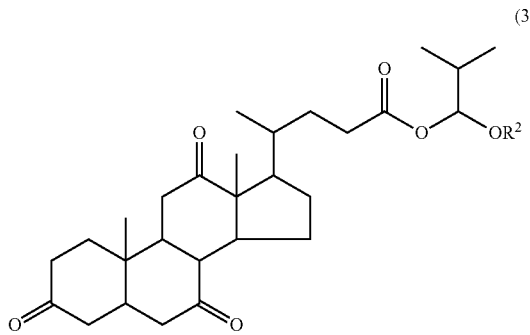

(3)

wherein $R^2$ is a straight, branched or cyclic alkyl group which may contain an oxygen atom and in which the sum of carbon and oxygen atoms is 1 to 15.

The chemically amplified positive resist composition is advantageously used in photolithography micropatterning since it is improved in resolution and minimized in LER.

A further embodiment of the invention is a pattern forming process comprising the steps of (i) coating the resist composition defined above onto a substrate and prebaking to form a resist film, (ii) exposing the resist film to high-energy radiation having a wavelength of up to 300 nm or electron beam through a photomask, and (iii) baking and developing with a developer to form a resist pattern.

The pattern forming process using the chemically amplified positive resist composition of the invention is successful in forming a resist pattern with a high resolution and a minimal LER and is best suited for photolithography micropatterning.

A still further embodiment of the invention is an acid-decomposable keto ester compound of steroid skeleton which is insoluble in alkaline developer, but turns soluble in alkaline developer under the action of acid, represented by the general formula (3):

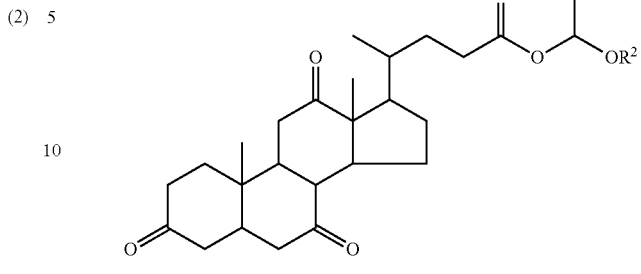

(3)

wherein $R^2$ is a straight, branched or cyclic alkyl group which may contain an oxygen atom and in which the sum of carbon and oxygen atoms is 1 to 15.

The acid-decomposable keto ester compound of steroid skeleton having formula (3) can be readily prepared in high yields by the method to be described later. When added in a proper amount to a chemically amplified positive resist composition, the compound is effective for providing the composition with a high resolution and a minimal LER. By a choice of optimum $R^2$ for a particular application, a balance of resist properties including pattern profile, resolution, and LER can be adjusted appropriate.

Advantageous Effects of Invention

The chemically amplified positive resist composition is improved in resolution and minimized in LER. The composition is useful in the lithography micropatterning using EB, deep-UV and EUV. The acid-decomposable keto ester compound of steroid skeleton is effective when added to a resist material adapted for the KrF, ArF, EUV, EB or x-ray lithography to form a micropatterning composition for the manufacture of VLSI. The resist composition is applicable to the immersion lithography as well as the conventional lithography.

DESCRIPTION OF EMBODIMENTS

The singular forms "a," an and the include plural referents unless the context clearly dictates otherwise. "Optional" or "optionally" means that the subsequently described event or circumstance may or may not occur, and that the description includes instances where the event occurs and instances where it does not. As used herein, the notation ($C_n$-$C_m$) means a group containing from n to m carbon atoms per group. The broken line depicted in a chemical formula denotes a valence bond.

The abbreviations and acronyms have the following meaning.
UV: ultraviolet radiation
deep-UV: deep ultraviolet
EUV: extreme ultraviolet
EB: electron beam
Mw: weight average molecular weight
Mn: number average molecular weight
Mw/Mn: molecular weight distribution or dispersity
GPC: gel permeation chromatography
PEB: post-exposure baking
LER: line edge roughness As used herein, the term "substantially insoluble" means that a polymer is insoluble or difficulty soluble in an alkaline developer.

The inventors sought for a compound capable of providing a chemically amplified positive resist composition with a high resolution and minimal LER when added thereto. The inventors have found that when an acid-decomposable keto ester compound of steroid skeleton having the general formula (1), preferably the general formula (2), and more preferably the general formula (3) is added to a chemically amplified positive resist composition, the resulting composition is given a high resolution and minimal LER.

In one embodiment, an acid-decomposable keto ester compound of steroid skeleton is added to a chemically amplified positive resist composition. One, two or more keto ester compounds may be used. Specifically the keto ester compound has the general formula (1).

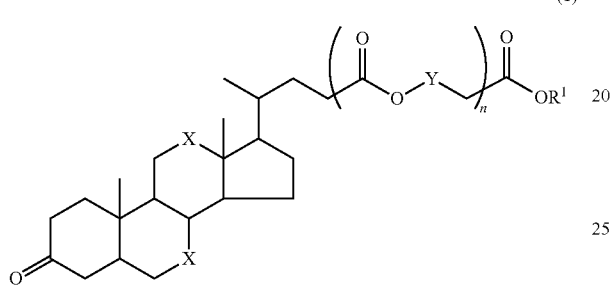

(1)

Herein $R^1$ is such an acid labile group having 6 to 20 carbon and oxygen atoms in total that —$COOR^1$ is decomposed to generate carboxyl under the action of acid, X is each independently a carbonyl group (—CO—) or methylene group (—$CH_2$—), Y is each independently a single bond or a $C_1$-$C_6$ alkylene group, and n is an integer of 0 to 2.

In formula (1), $R^1$ is such an acid labile group that —$COOR^1$ is decomposed to generate carboxyl under the action of acid. In the acid labile group $R^1$, the sum of carbon and oxygen atoms is 6 to 20. The acid labile group may contain a multiple bond, or a hydroxyl, carbonyl, ester or ether moiety. If the sum of carbon and oxygen atoms in $R^1$ is less than 6, problems may arise that a chemically amplified positive resist composition having the keto ester compound added thereto has degraded resolution due to insufficient dissolution contrast, and that defects are formed upon coating due to poor solubility in solvent of the keto ester compound. If the sum of carbon and oxygen atoms in $R^1$ exceeds 20, problems may arise that a chemically amplified positive resist composition having the keto ester compound added thereto has degraded resolution due to excessive acid diffusion, and that the pattern becomes less rectangular. Examples of acid labile group $R^1$ include the following structures, but are not limited thereto. Notably the broken line denotes a valence bond.

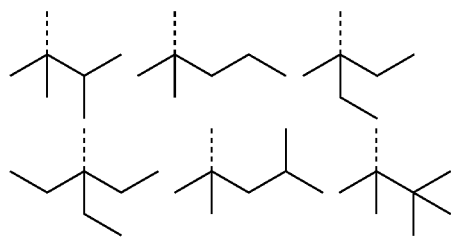

-continued

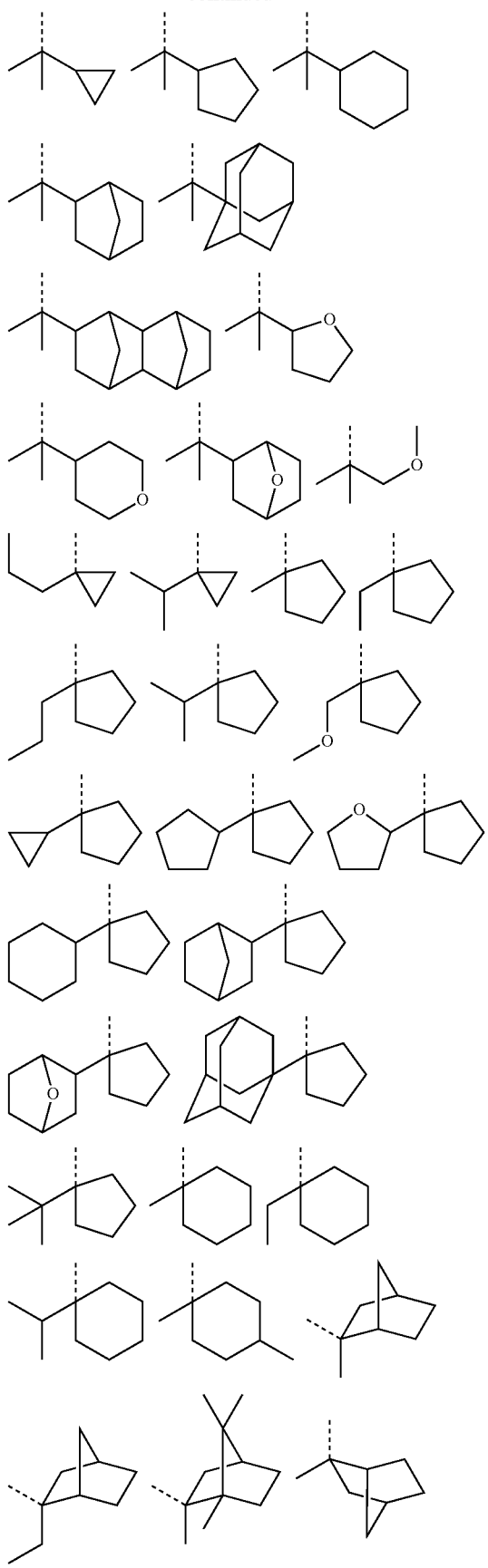

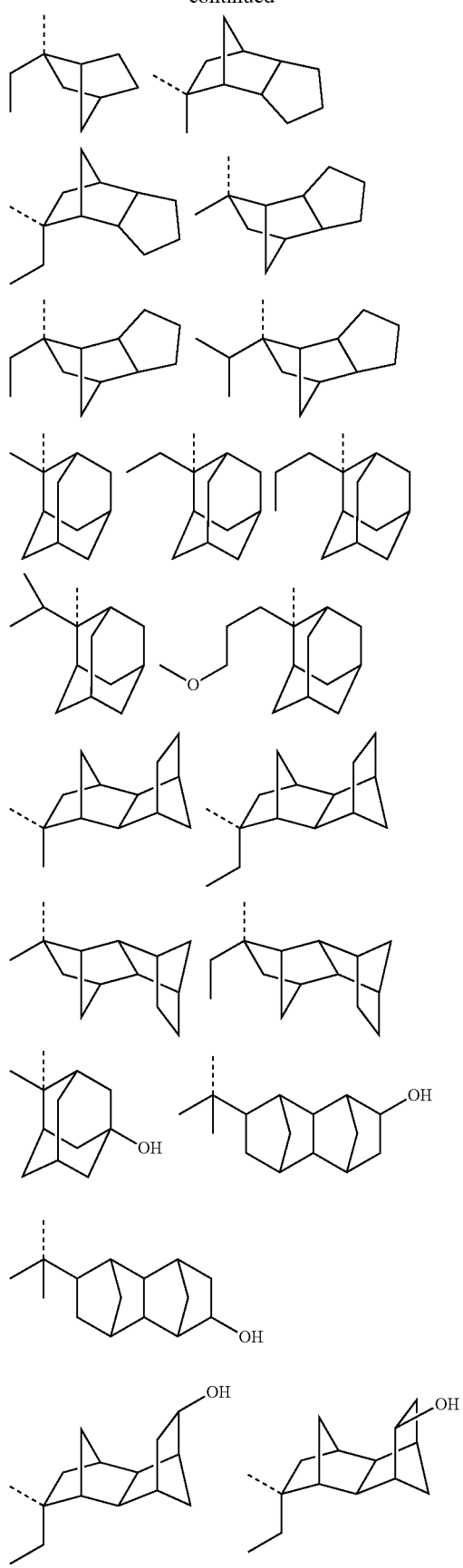
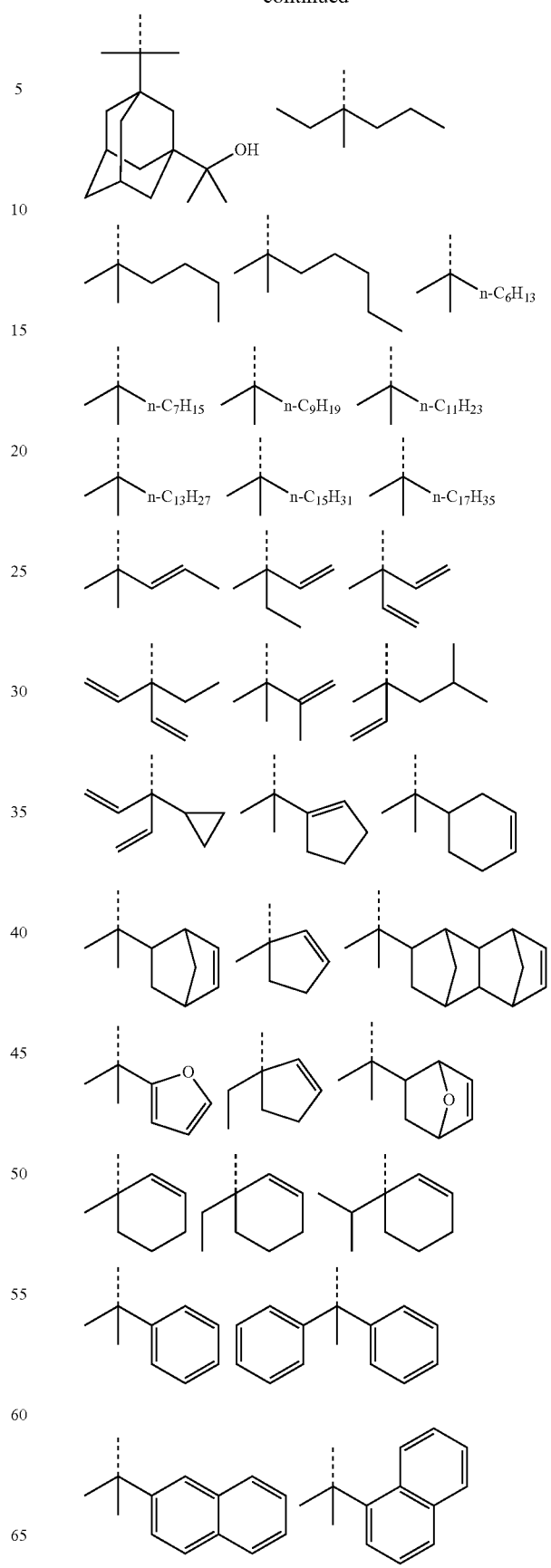

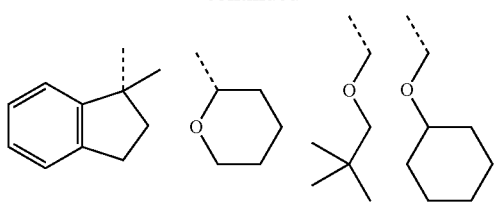
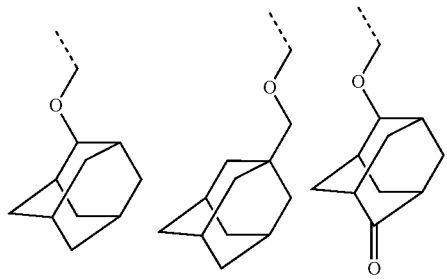
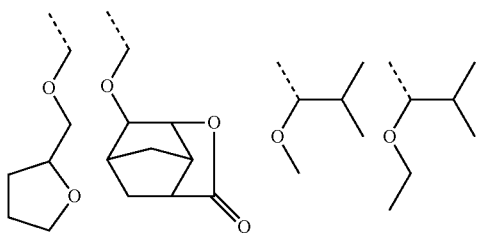
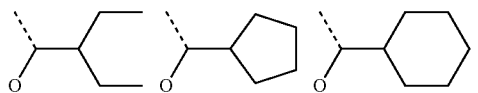
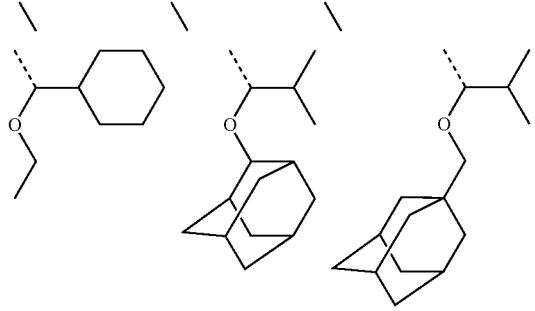
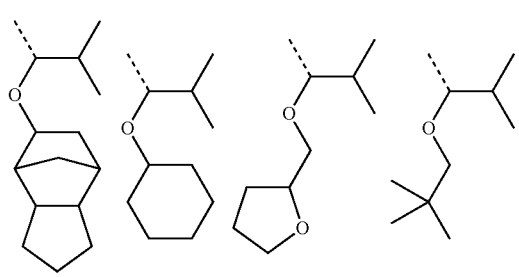
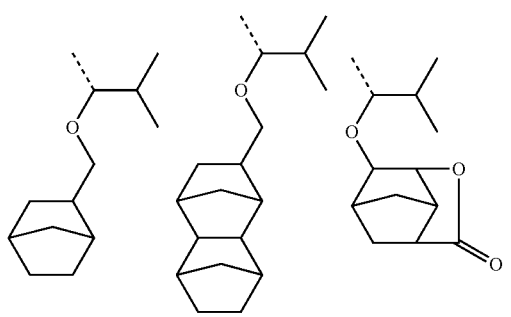

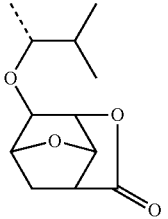

In formula (1), X is each independently a carbonyl group (—CO—) or methylene group (—CH$_2$—). Preferably, two X's are both carbonyl (—CO—). Y is each independently a single bond or a C$_1$-C$_6$ alkylene group, and preferably a single bond. Examples of Y include, but are not limited to, a single bond, methylene, ethylene, trimethylene, tetramethylene, pentamethylene, hexamethylene, propylene, ethylethylene, ethylidene, and isopropylidene. The subscript n is an integer of 0 to 2, preferably n=0 or 1, and most preferably n=0.

Examples of the acid-decomposable keto ester compound of steroid skeleton having formula (1) include, but are not limited to, the following compounds as well as examples of the compounds having formulae (2) and (3) which will be illustrated later.

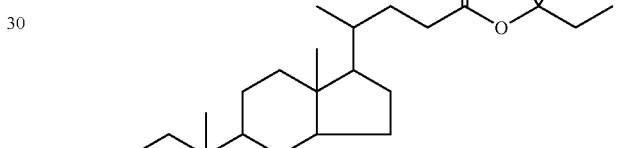
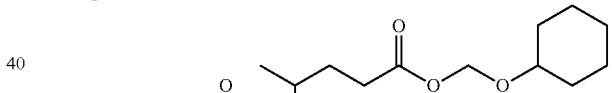
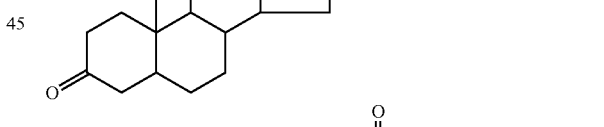
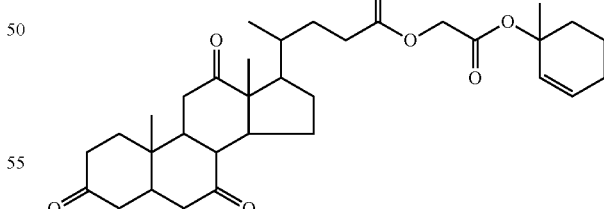
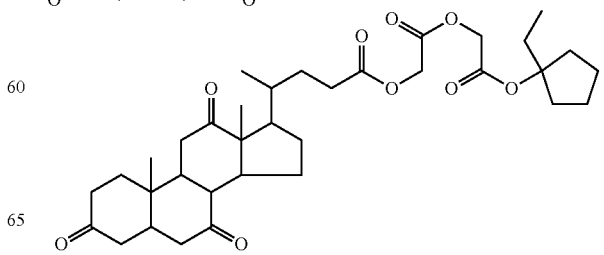

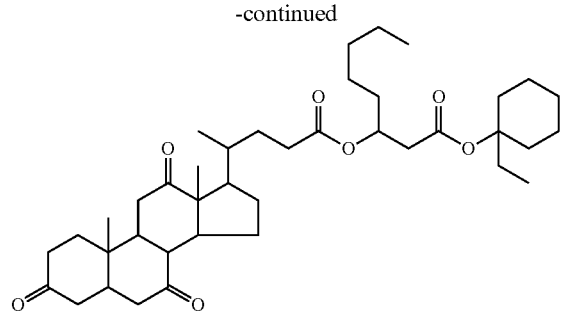

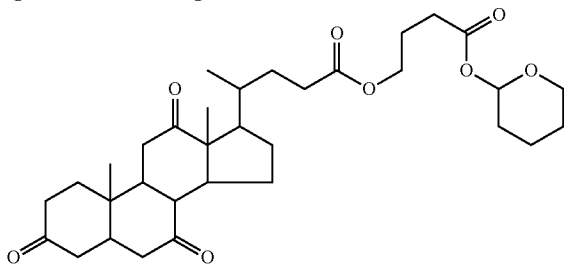

Preferably the acid-decomposable keto ester compound of steroid skeleton having formula (1) to be added to the chemically amplified positive resist composition of the invention is an acid-decomposable keto ester compound of steroid skeleton having the general formula (2):

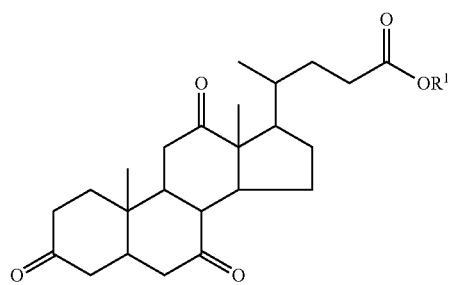

(2)

wherein $R^1$ is such an acid labile group having 6 to 20 carbon and oxygen atoms in total that —COOR$^1$ is decomposed to generate carboxyl under the action of acid. In formula (2), $R^1$ is as defined and illustrated above.

Examples of the acid-decomposable keto ester compound of steroid skeleton having formula (2) include, but are not limited to, the following compounds as well as examples of the compound having formula (3) which will be illustrated later.

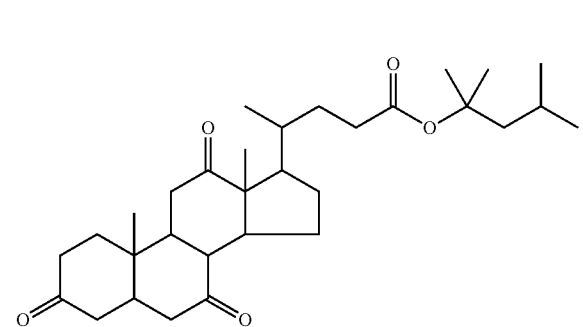

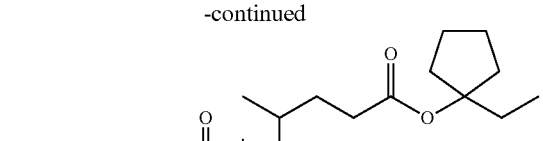

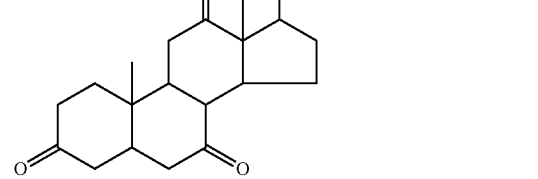

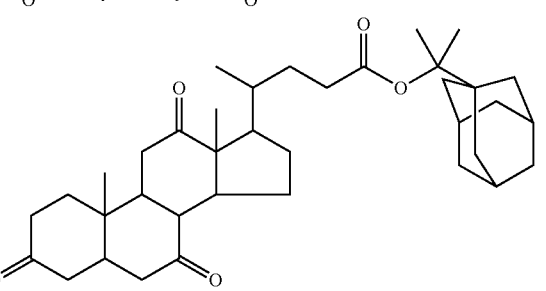

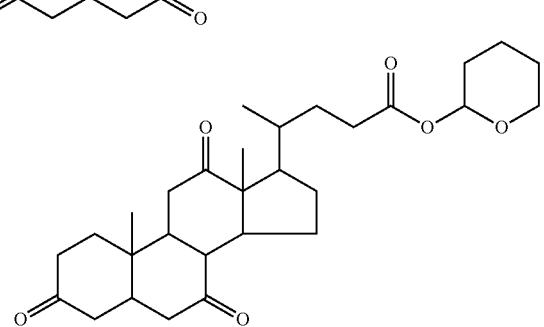

-continued

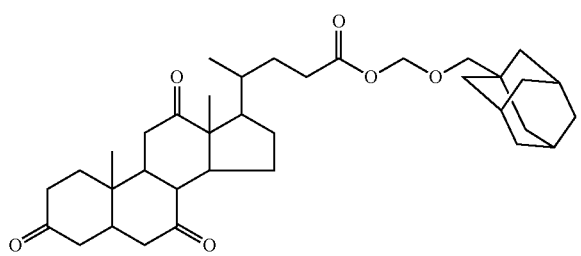

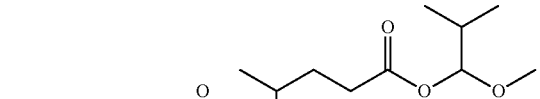

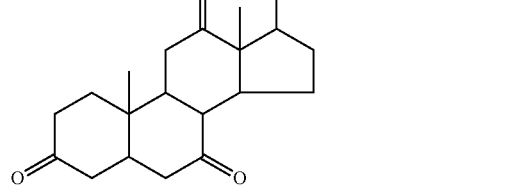

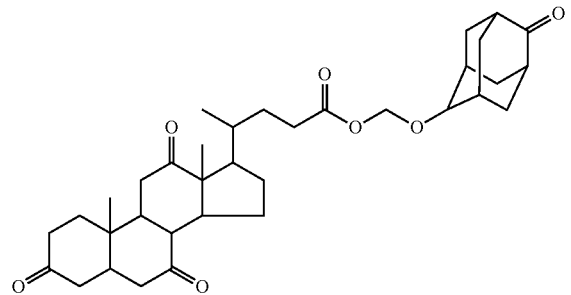

More preferably the acid-decomposable keto ester compound of steroid skeleton having formula (1) or (2) to be added to the chemically amplified positive resist composition of the invention is an acid-decomposable keto ester compound of steroid skeleton having the general formula (3):

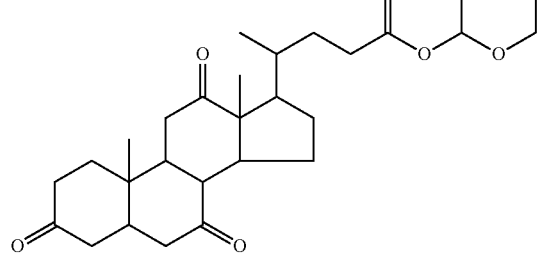

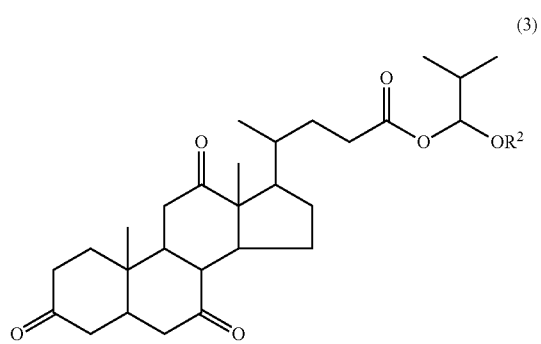

(3)

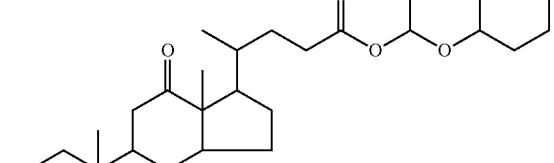

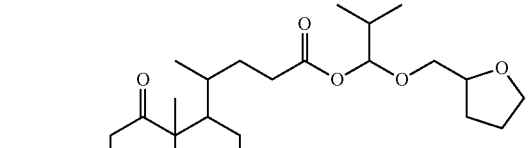

wherein $R^2$ is a straight, branched or cyclic alkyl group which may contain an oxygen atom and in which the sum of carbon and oxygen atoms is 1 to 15. The acid-decomposable keto ester compound of steroid skeleton having formula (3) is extraordinarily effective for improving resolution and LER when added to resist compositions.

In formula (3), $R^2$ is a straight, branched or cyclic alkyl group which may contain an oxygen atom and in which the sum of carbon and oxygen atoms is 1 to 15. Herein oxygen may intervene in an alkylene chain or oxygen may be contained in the form of carbonyl group. Examples of $R^2$ include, but are not limited to, methyl, ethyl, propyl, isopropyl, butyl, isobutyl, s-butyl, t-butyl, pentyl, neopentyl, cyclopentyl, hexyl, cyclohexyl, 2-ethylhexyl, decyl, pentadecyl, adamantyl, norbornyl, norbornylmethyl, tricyclodecanyl, tetracyclododecanyl, tetracyclododecanylmethyl, benzyl, and tetrahydrofurfuryl.

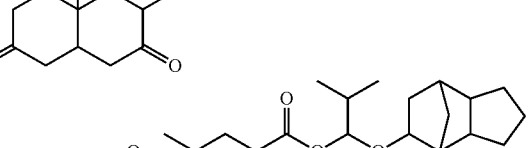

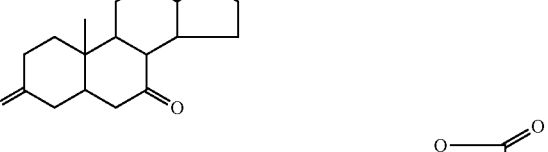

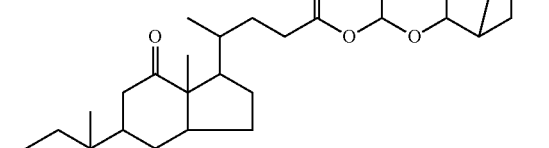

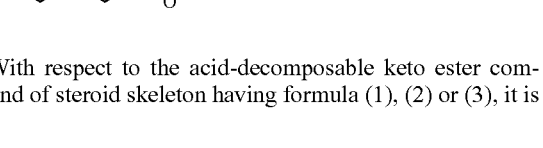

Examples of the acid-decomposable keto ester compound of steroid skeleton having formula (3) include, but are not limited to, the following compounds.

With respect to the acid-decomposable keto ester compound of steroid skeleton having formula (1), (2) or (3), it is believed that the presence of steroid skeleton contributes to the exertion of inhibitory dissolution and etch resistance. The presence of keto group (carbonyl group) imparts appropriate polarity and hydrophilicity to the molecule and provides affinity to and compatibility with the base resin, thus contributing to LER improvement. In addition, the keto group has an appropriate affinity to the acid generated by the acid generator and is believed to be effective for controlling acid diffusion. If the keto group is absent, and a methylene group or ester group is present instead, acid diffusion control becomes insufficient, often leading to a likelihood of degrading resolution as the feature size is reduced. If a hydroxyl group is present instead of the keto group, it may lead to excessive hydrophilicity, less inhibitory dissolution, a drop of dissolution contrast, and degraded resolution. The presence of acid-decomposable group within the molecule is essential for a dissolution contrast. The acid-decomposable group contributes to resolution improvement in that under the action of the acid generated by the acid generator in the exposed area of resist film, the acid-decomposable group is decomposed to generate a carboxylic acid whereby the compound increases its solubility in alkaline developer. By selecting appropriate ones for $R^1$, $R^2$, Y and n in formula (1), (2) or (3) from their possible ranges, properties of the acid-decomposable keto ester compound of steroid skeleton having formula (1), (2) or (3) including dissolution inhibition, dissolution contrast, decomposition reactivity, polarity, hydrophilicity, diffusion rate, solvent solubility, acid affinity, and base resin compatibility can be adjusted in accordance with a particular base resin, acid generator and lithography method used. Eventually the pattern profile and other performance factors of the resist composition can be adjusted optimum.

The acid-decomposable keto ester compound of steroid skeleton having formula (1), (2) or (3) may be used in different ways, for example, as a molecular resist based on this keto ester compound or as a dissolution inhibitor in combination with a polymer having an acid labile group which turns alkali soluble under the action of acid.

The acid-decomposable keto ester compound of steroid skeleton having formula (3) can be prepared by selecting an optimum method in accordance with the structure of the compound. Suitable methods include, but are not limited to, O-alkylation reaction of dehydrocholic acid using a halide and addition reaction of dehydrocholic acid to a vinyl ether compound. These methods are described below in detail.

The first method, O-alkylation reaction of dehydrocholic acid using a halide runs according to the following scheme:

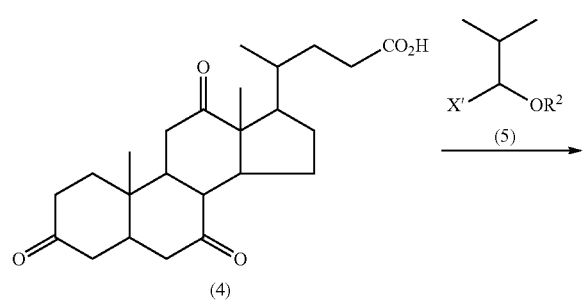

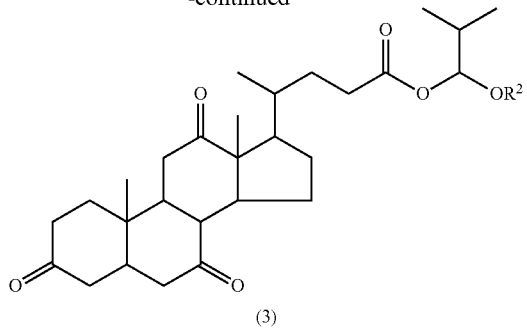

Herein $R^2$ is as defined above, and X' is halogen.

The halide (5) serves as the O-alkylating agent in the present reaction, wherein X' is halogen, with chlorine being most preferable from the industrial standpoint of shelf stability of the halide (5). The halide (5) is desirably used in an amount of 0.5 to 5 moles, more desirably 0.9 to 2 moles per mole of dehydrocholic acid (4). Reaction is desirably carried out in a solvent. Suitable reaction solvents include hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform and 1,2-dichloroethylene; aprotic polar solvents such as N,N-dimethylformamide, N,N-dimethylacetamide, dimethyl sulfoxide, and N-methylpyrrolidone; esters such as ethyl acetate and butyl acetate; ketones such as acetone and 2-butanone; nitriles such as acetonitrile; amines such as pyridine and triethylamine; alcohols such as isopropyl alcohol and t-butyl alcohol; and water. A suitable solvent or solvents may be selected and used alone or in admixture, depending on reaction conditions. The reaction temperature may be selected in the range from 0° C. to the reflux temperature of the solvent, depending on the desired reaction rate. If desired, a base may be added to the reaction system. Examples of the base include amines such as pyridine, triethylamine, diisopropylethylamine, 4-dimethylaminopyridine, and imidazole; metal alkoxides such as sodium methoxide, sodium ethoxide, and potassium t-butoxide; carbonates such as sodium carbonate, potassium carbonate, and cesium carbonate; hydroxides such as sodium hydroxide, potassium hydroxide, and tetramethylammonium hydroxide; metal hydrides such as sodium hydride and potassium hydride; organometallics such as butyl lithium and ethyl magnesium bromide; and metal amides such as lithium diisopropyl amide. A suitable base or bases may be selected and used alone or in admixture, depending on reaction conditions. The base is desirably used in an amount of 0.1 to 10 moles, more desirably 0.9 to 5 moles per mole of dehydrocholic acid (4).

If desired for accelerating the reaction rate, a catalyst may be added to the reaction system. Suitable catalysts include iodides such as sodium iodide, lithium iodide, and tetrabutylammonium iodide, and bromides such as sodium bromide, lithium bromide, and tetrabutylammonium bromide. When added, the catalyst is desirably used in an amount of 0.001 to 2 moles, more desirably 0.005 to 0.5 mole per mole of dehydrocholic acid (4). The reaction time is determined as appropriate by monitoring the reaction process by liquid chromatography (LC) or thin-layer chromatography (TLC) because it is desirable from the yield aspect to drive the reaction to completion. Usually the reaction time is about 0.5 to about 24 hours. The desired compound (3) may be obtained from the reaction mixture by ordinary aqueous work-up. If necessary, the compound may be purified by standard techniques like chromatography and recrystallization. Alternatively, the aqueous work-up is omitted, and the reaction solution may be purified directly or after filtration of the salt resulting from reaction.

The second method, addition reaction of dehydrocholic acid to a vinyl ether compound runs according to the following scheme.

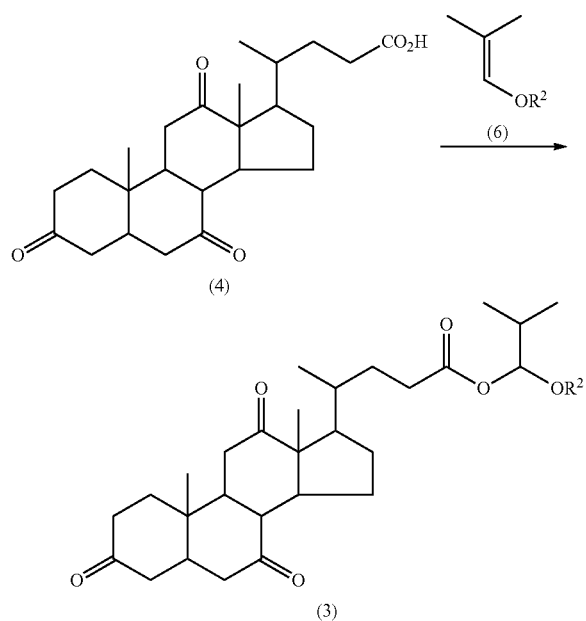

Herein R² is as defined above.

The vinyl ether compound (6) is desirably used in an amount of 0.5 to 10 moles, more desirably 0.9 to 5 moles per mole of dehydrocholic acid (4). Reaction is desirably carried out in a solvent. Suitable reaction solvents include hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform and 1,2-dichloroethylene; aprotic polar solvents such as N,N-dimethylformamide, N,N-dimethylacetamide, dimethyl sulfoxide, and N-methylpyrrolidone; esters such as ethyl acetate and butyl acetate; ketones such as acetone and 2-butanone; and nitriles such as acetonitrile. A suitable solvent or solvents may be selected and used alone or in admixture, depending on reaction conditions. The reaction temperature may be selected in the range from 0° C. to the reflux temperature of the solvent, depending on the desired reaction rate. If desired, an acid catalyst may be added to the reaction system. Examples of the acid catalyst include mineral acids such as sulfuric acid, hydrochloric acid, phosphoric acid and perchloric acid; Lewis acids such as boron trifluoride, boron trifluoride diethyl ether complex, dibutyltin oxide, aluminum chloride, zinc chloride, tetrachlorotitanium, and tetramethoxytitanium; sulfonic acids such as methanesulfonic acid and p-toluenesulfonic acid; salts such as potassium hydrogen sulfate, calcium chloride, magnesium chloride, and pyridinium p-toluenesulfonate; carboxylic acids such as oxalic acid and trifluoroacetic acid; and acidic resins such as cation exchange resins. A suitable catalyst or catalysts may be selected and used alone or in admixture, depending on reaction conditions. The catalyst is desirably used in an amount of 0.1 to 10 moles, more desirably 0.9 to 5 moles per mole of dehydrocholic acid (4).

The reaction time is determined as appropriate by monitoring the reaction process by liquid chromatography (LC) or thin-layer chromatography (TLC) because it is desirable from the yield aspect to drive the reaction to completion. Usually the reaction time is about 0.5 to about 24 hours. The desired compound (3) may be obtained from the reaction mixture by ordinary aqueous work-up. If necessary, the compound may be purified by standard techniques like chromatography and recrystallization. Alternatively, the reaction solution may be directly purified in some cases, without the aqueous work-up.

The acid-decomposable keto ester compound of steroid skeleton defined above is used to formulate a resist composition, typically a chemically amplified positive resist composition. Specifically the resist composition is defined as comprising (A) one or more acid-decomposable keto ester compound of steroid skeleton which is insoluble in alkaline developer, but turns soluble in alkaline developer under the action of acid, represented by formula (1), (2) or (3), (B) an organic solvent, (C) a base resin having an acidic functional group protected with an acid labile group, which is substantially insoluble in alkaline developer, but turns soluble in alkaline developer when the acid labile group is decomposed, (D) an acid generator as essential components, (E) a quencher and (F) a surfactant as optional components.

Component (A) is preferably used in an amount of 0.5 to 100 parts, more preferably 1 to 30 parts by weight per 100 parts by weight of the base resin (C). Outside the range, a less amount of component (A) may fail to exert the addition effect whereas an excessive amount may adversely affect film formation. Component (A) may be used alone or in admixture of two or more.

The organic solvent (B) used herein may be any organic solvent in which the keto ester compound (A), base resin (C), acid generator (D), and other components are soluble. Illustrative, non-limiting, examples of the organic solvent include ketones such as cyclopentanone, cyclohexanone, 4-methyl-2-pentanone, and methyl amyl ketone; alcohols such as 3-methoxybutanol, 3-methyl-3-methoxybutanol, 1-methoxy-2-propanol, 1-ethoxy-2-propanol, n-propanol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, and cyclohexanol; ethers such as propylene glycol monomethyl ether, ethylene glycol monomethyl ether, propylene glycol monoethyl ether, ethylene glycol monoethyl ether, propylene glycol dimethyl ether, diethylene glycol dimethyl ether, methyl cyclopentyl ether, methyl cyclohexyl ether, anisole, diisopropyl ether, diisobutyl ether, diisopentyl ether, di-n-pentyl ether, methyl cyclopentyl ether, methyl cyclohexyl ether, di-n-butyl ether, di-sec-butyl ether, diisopentyl ether, di-sec-pentyl ether, di-t-amyl ether, and di-n-hexyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; and carbonates such as ethylene carbonate and propylene carbonate. These solvents may be used alone or in combinations of two or more. Of the above organic solvents, it is recommended to use propylene glycol monomethyl ether, PGMEA, cyclohexanone, γ-butyrolactone, ethyl lactate, and mixtures thereof because the base resin and acid generator are most soluble therein.

An appropriate amount of the organic solvent used may be determined in accordance with the desired film thickness or the like and is preferably 200 to 15,000 parts, more preferably 400 to 8,000 parts by weight per 100 parts by weight of the base resin.

Polymers used as the base resin (C) include polyhydroxystyrene (PHS), and copolymers of hydroxystyrene with styrenes, (meth)acrylic acid esters or other polymerizable olefinic compounds, for KrF excimer laser resist uses; (meth)acrylic acid ester polymers, alternating copolymers of cycloolefin with maleic anhydride, similar alternating copolymers further containing vinyl ethers or (meth)acrylic acid esters, polynorbornene, and polymers obtained from ring-opening metathesis polymerization (ROMP) of cycloolefins, for ArF excimer laser resist use; and fluorinated forms of the foregoing polymers (for both KrF and ArF laser uses) and polymers resulting from ring-closure polymerization using fluorinated dienes for $F_2$ laser resist use. Silicon-substituted forms of the foregoing polymers and polysilsesquioxane polymers are useful for the bilayer resists. The base polymer is not limited to these polymer systems. The base polymers may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The acid labile groups to be introduced into the base polymers may be selected from a variety of such groups, preferably from acetal groups of 2 to 30 carbon atoms and tertiary alkyl groups of 4 to 30 carbon atoms having the formulae (C1) and (C2), respectively.

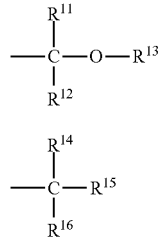

t-butoxymethyl, neopentyloxymethyl, (1-methylcyclohexyl)methoxymethyl, 2-adamantyloxymethyl, (1-adamantyl)methoxymethyl, phenethyloxymethyl, (2-methyl-2-norbornyl)methoxymethyl, 1-methoxyethyl, 1-methoxypropyl, 1-methoxybutyl, 1-ethoxyethyl, 1-ethoxypropyl, 1-ethoxybutyl, 1-propoxyethyl, 1-propoxypropyl, 1-propoxybutyl, 1-cyclopentyloxyethyl, 1-cyclohexyloxyethyl, 2-methoxyisopropyl, 2-ethoxyisopropyl, 1-phenoxyethyl, 1-benzyloxyethyl, 1-phenoxypropyl, 1-benzyloxypropyl, 1-adamantyloxyethyl, 1-adamantyloxypropyl, 2-tetrahydrofuryl, 2-tetrahydro-2H-pyranyl, 1-(2-cyclohexanecarbonyloxyethoxy)ethyl, 1-(2-cyclohexanecarbonyloxyethoxy)propyl, 1-[2-(1-adamantylcarbonyloxy)ethoxy]ethyl, and 1-[2-(1-adamantylcarbonyloxy)ethoxy]propyl.

Illustrative examples of the tertiary alkyl group of formula (C2) include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

In the base resin, some hydroxyl groups may be linked via acid labile groups of the following general formula (C3a) or (C3b) for crosslinkage between molecules or within a molecule.

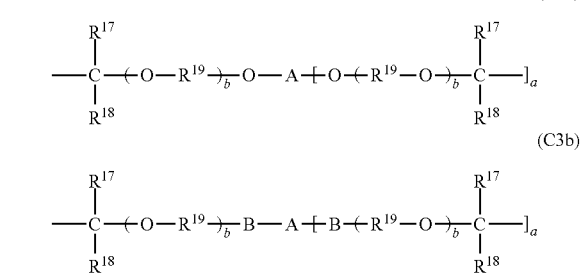

In formulae (C1) and (C2), $R^{11}$ and $R^{12}$ each are hydrogen or a straight, branched or cyclic alkyl group of 1 to 20 carbon atoms, preferably 1 to 12 carbon atoms, which may contain a heteroatom such as oxygen, sulfur, nitrogen or fluorine, $R^{13}$, $R^{14}$, $R^{15}$ and $R^{15}$ each are a straight, branched or cyclic alkyl group, aryl group or aralkyl group of 1 to 20 carbon atoms, preferably 1 to 12 carbon atoms, which may contain a heteroatom such as oxygen, sulfur, nitrogen or fluorine. A pair of $R^{11}$ and $R^{12}$, a pair of $R^{11}$ and $R^{13}$, a pair of $R^{12}$ and $R^{13}$, a pair of $R^{14}$ and $R^{15}$, a pair of $R^{14}$ and $R^{15}$, or a pair of $R^{15}$ and $R^{15}$, taken together, may form a non-aromatic ring of 3 to 20 carbon atoms, preferably 3 to 12 carbon atoms, with the carbon or oxygen atom to which they are attached.

Illustrative examples of the acetal group of formula (C1) include, but are not limited to, methoxymethyl, ethoxymethyl, propoxymethyl, butoxymethyl, isopropoxymethyl, Herein, $R^{17}$ and $R^{18}$ each are hydrogen or a straight, branched or cyclic $C_1$-$C_8$ alkyl group, or $R^{17}$ and $R^{18}$, taken together, may form a ring with the carbon atom to which they are attached. Each of $R^{17}$ and $R^{18}$ is a straight or branched $C_1$-$C_8$ alkylene group when they form a ring. $R^{19}$ is a straight, branched or cyclic $C_1$-$C_{10}$ alkylene group. Letter "a" is an integer of 1 to 7, and "b" is 0 or an integer of 1 to 10. "A" is a (a+1)-valent aliphatic or alicyclic saturated hydrocarbon group, aromatic hydrocarbon group or heterocyclic group of 1 to 50 carbon atoms, which may have an intervening heteroatom and in which some hydrogen atoms may be replaced by hydroxyl, carboxyl or carbonyl radicals or fluorine atoms. B is —CO—O—, —NHCO—O— or —NHCONH—.

Illustrative examples of the crosslinking acetal linkages represented by formulae (C3a) and (C3b) are given below as (C3)-1 through (C3)-8, but not limited thereto.

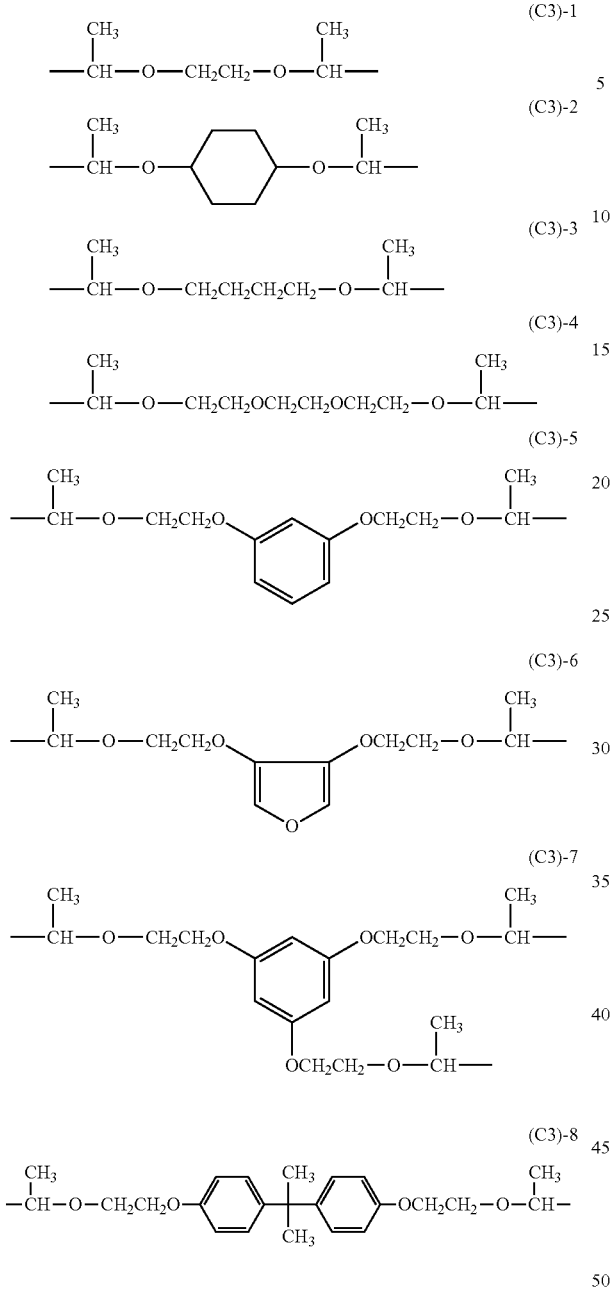

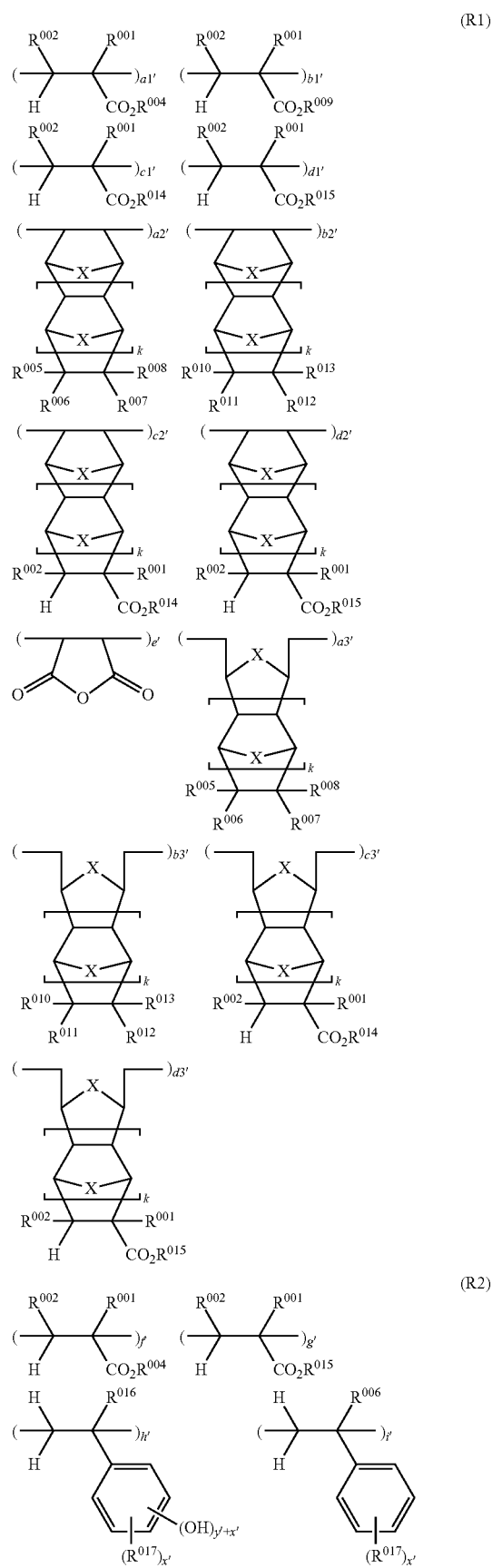

Preferably the base polymer has a weight average molecular weight (Mw) of 2,000 to 100,000 as measured by GPC versus polystyrene standards using tetrahydrofuran solvent. With Mw below 2,000, film formation and resolution may become poor. With Mw beyond 100,000, resolution may become poor or foreign matter may generate during pattern formation.

In the embodiment wherein the chemically amplified positive resist composition is used as the resist material for the ArF excimer laser lithography, the preferred base resins include those resins described in U.S. Pat. No. 7,537,880 (JP-A 2008-111103, paragraphs [0072]-[0121]).

Specifically, those polymers comprising units of the following formula (R1) and/or (R2) are preferred.

-continued

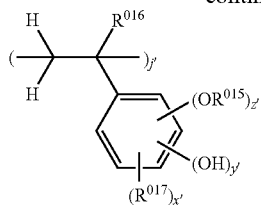

Herein, $R^{001}$ is hydrogen, methyl or $CH_2CO_2R^{003}$.

$R^{002}$ is hydrogen, methyl or $CO_2R^{003}$.

$R^{003}$ is a straight, branched or cyclic $C_1$-$C_{15}$ alkyl group, examples of which include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl.

$R^{004}$ is hydrogen or a monovalent hydrocarbon group of 1 to 15 carbon atoms having at least one group selected from among fluorinated substituent groups, carboxyl groups and hydroxyl groups. Examples include hydrogen, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, hydroxyadamantyl, hydroxyhexafluoroisopropylcyclohexyl, and di(hydroxyhexafluoroisopropyl)cyclohexyl.

At least one of $R^{005}$ to $R^{008}$ represents a monovalent hydrocarbon group of 1 to 15 carbon atoms having at least one group selected from among fluorinated substituent groups, carboxyl groups and hydroxyl groups while the remaining R's independently represent hydrogen or straight, branched or cyclic $C_1$-$C_{15}$ alkyl groups. Examples of suitable monovalent $C_1$-$C_{15}$ hydrocarbon groups having at least one group selected from among fluorinated substituent groups, carboxyl groups and hydroxyl groups include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, hydroxyadamantyloxycarbonyl, hydroxyhexafluoroisopropylcyclohexyloxycarbonyl, and di(hydroxyhexafluoroisopropyl)cyclohexyloxycarbonyl. Suitable straight, branched or cyclic $C_1$-$C_{15}$ alkyl groups are as exemplified for $R^{003}$.

Two of $R^{005}$ to $R^{008}$ example, a pair of $R^{005}$ and $R^{006}$, or $R^{006}$ and $R^{007}$) may bond together to form a ring with the carbon atom(s) to which they are attached, and in that event, at least one of $R^{005}$ to $R^{008}$ is a divalent hydrocarbon group of 1 to 15 carbon atoms having at least one group selected from fluorinated substituent groups, carboxyl groups and hydroxyl groups, while the remaining R's are independently single bonds or straight, branched or cyclic $C_1$-$C_{15}$ alkylene groups. Suitable divalent $C_1$-$C_{15}$ hydrocarbon groups having at least one group selected from fluorinated substituent groups, carboxyl groups and hydroxyl groups include those exemplified above as the monovalent hydrocarbon groups having at least one group selected from fluorinated substituent groups, carboxyl groups and hydroxyl groups, with one hydrogen atom eliminated therefrom. Suitable straight, branched or cyclic $C_1$-$C_{15}$ alkylene groups are those groups exemplified for $R^{003}$, with one hydrogen atom eliminated therefrom.

$R^{009}$ is a monovalent hydrocarbon group of 3 to 15 carbon atoms containing a —$CO_2$— partial structure. Examples include 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $8^{010}$ to $R^{013}$ is a monovalent hydrocarbon group of 2 to 15 carbon atoms containing a —$CO_2$— partial structure, while the remaining R's are independently hydrogen atoms or straight, branched or cyclic $C_1$-$C_{15}$ alkyl groups. Illustrative examples of suitable monovalent $C_2$-$C_{15}$ hydrocarbon groups containing a —$CO_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Suitable straight, branched or cyclic $C_1$-$C_{15}$ alkyl groups are as exemplified for $R^{003}$.

Two of $R^{010}$ to $R^{013}$ (for example, a pair of $R^{010}$ and $R^{011}$, or $R^{011}$ and $R^{012}$) may bond together to form a ring with the carbon atom(s) to which they are attached, and in that event, at least one of $R^{010}$ to $R^{013}$ is a divalent hydrocarbon group of 1 to 15 carbon atoms containing a —$CO_2$— partial structure, while the remaining R's are independently single bonds or straight, branched or cyclic $C_1$-$C_{15}$ alkylene groups. Illustrative examples of suitable divalent $C_1$-$C_{15}$ hydrocarbon groups containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as those exemplified as the monovalent hydrocarbon groups containing a —$CO_2$— partial structure, with one hydrogen atom eliminated therefrom. Suitable straight, branched or cyclic $C_1$-$C_{15}$ alkylene groups are those groups exemplified for $R^{003}$, with one hydrogen atom eliminated therefrom.

$R^{014}$ is a polycyclic hydrocarbon group having 7 to 15 carbon atoms or an alkyl group containing such a polycyclic hydrocarbon group. Examples include norbornyl, bicyclo[3.3.1]nonyl, tricyclo[5.2.1.0$^{2,6}$]decyl, adamantyl, ethyladamantyl, butyladamantyl, norbornylmethyl, and adamantylmethyl.

$R^{015}$ is an acid labile group, examples of which will be described later.

$R^{016}$ is hydrogen or methyl.

$R^{017}$ is a straight, branched or cyclic $C_1$-$C_8$ alkyl group.

X is $CH_2$ or an oxygen atom. Letter k is 0 or 1.

In formula (R1), letters a1', a2', a3', b1', b2', b3', c1', c2', c3', d1', d2', d3', and e' are numbers from 0 to less than 1, satisfying a1'+a2'+a3'+b1'+b2'+b3'+c1'+c2'+c3'+d1'+d2'+d3'+e'=1. In formula (R2), letters f', g', h', i', and j' are numbers from 0 to less than 1, satisfying f'+g'+h'+i'+j'=1; x', y' and z' are each an integer of 0 to 3, satisfying 1≦x'+y'+z'≦5 and 1≦y'+z'≦3.

The acid labile group represented by $R^{015}$ may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

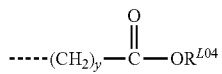 (L2)

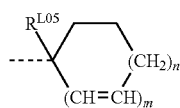 (L3)

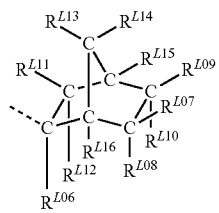 (L4)

In these formulae, the broken line denotes a valence bond. In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Suitable straight, branched or cyclic alkyl groups are as exemplified for $R^{L01}$ and $R^{L02}$, and suitable substituted alkyl groups are shown below.

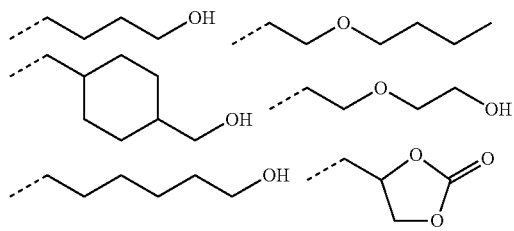

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of participant $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups include trimethylsilyl, triethylsilyl and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic $C_1$-$C_{10}$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, substituted forms of such groups in which some hydrogen atoms are substituted by hydroxyl, alkoxy, carboxyl, alkoxycarbonyl, oxo, amino, alkylamino, cyano, mercapto, alkylthio, sulfo or other groups, and similar groups in which one or more methylene moiety is replaced by oxygen or sulfur atom. Examples of the optionally substituted aryl groups include phenyl, methylphenyl, naphthyl, anthryl, phenanthryl, and pyrenyl. Letter m is equal to 0 or 1, n is equal to 0, 1, 2 or 3, and 2 m+n is equal to 2 or 3.

In formula (L4), $R_{L06}$ is a substituted or unsubstituted, straight, branched or cyclic $C_1$-$C_{10}$ alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$, and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

An acid generator, typically photoacid generator (PAG) is used herein as component (D). It is any compound capable of generating an acid upon exposure to high-energy radiation such as UV, deep-UV, EB, x-ray, excimer laser, gamma-ray, and synchrotron radiation. Suitable photoacid generators include sulfonium salt, iodonium salt, sulfonyldiazomethane, N-sulfonyloxydicarboxylmide, O-arylsulfonyloxime, and O-alkylsulfonyloxime acid generators. The acid generators may be used alone or in admixture of two or more. Exemplary acid generators are described in U.S. Pat. No. 7,537,880 (JP-A 2008-111103, paragraphs [0122]-[0142]).

Inter alia, acid generators having the general formula (PAG-A) are preferred. These acid generators may be used in combination with other acid generators.

 (PAG-A)

Herein Ar is a substituted or unsubstituted $C_6$-$C_{20}$ aryl group which may contain a halogen, oxygen, nitrogen or sulfur atom. $R^{PC}$ is Ar, or a straight, branched or cyclic $C_1$-$C_{20}$ alkyl group which may contain a halogen, oxygen, nitrogen or sulfur atom, or two $R^{PC}$ may bond together to form a ring of 5 to 8 carbon atoms with the sulfur atom to which they are attached at their terminus. $R^{PA}$ is a straight, branched or cyclic $C_{10}$-$C_{50}$ alkyl group which may contain a halogen, oxygen, nitrogen or sulfur atom, a substituted or unsubstituted $C_6$-$C_{30}$ aryl group which may contain a halogen, oxygen, nitrogen or sulfur atom, a substituted or unsubstituted $C_7$-$C_{30}$ aralkyl group which may contain a halogen, oxygen, nitrogen or sulfur atom, —$C_nF_{(2n+1)}$, $R^{PA1}CO_2CH(R^{PA2})$—, or $R^{PA1}OC(O)$— wherein n is an integer of 0 to 10. Inter alia, $R^{PA1}CO_2CH(R^{PA2})$— is most preferred because of improved resolution of fine lines. $R^{PA1}$ is a straight, branched or cyclic $C_{10}$-$C_{50}$ alkyl group which may contain a halogen, oxygen, nitrogen or sulfur atom, a substituted or unsubstituted $C_6$-$C_{30}$ aryl group which may contain a halogen, oxygen, nitrogen or sulfur atom, or a substituted or unsubstituted $C_7$-$C_{30}$ aralkyl group which may contain a halogen, oxygen, nitrogen or sulfur atom. $R^{PA2}$ is hydrogen or trifluoromethyl.

In the resist composition, the PAG may be added in any desired amount as long as the objects of the invention are not compromised. An appropriate amount of the PAG is 0.1 to 80 parts, and more preferably 1 to 40 parts by weight per 100 parts by weight of the base resin in the composition. Too high a proportion of the PAG may give rise to problems of degraded resolution and foreign matter upon development and resist film peeling. The PAG may be used alone or in admixture of two or more. The transmittance of the resist film can be controlled by using an PAG having a low transmittance at the exposure wavelength and adjusting the amount of the PAG added.

One or more quenchers (E) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, aromatic amines, heterocyclic amines, nitrogen-containing compounds with carboxyl group, nitrogen-containing compounds with hydroxyl group, N-oxides, amides, imides, carbamates, and ammonium salts.

Any of the foregoing compounds may be used as the quencher as long as they have the desired effect. Useful quenchers include basic compounds and nitrogen-containing organic compounds described in the following patent documents.

| | | |
|---|---|---|
| JP-A H11-084639 | JP-A 2001-166476 | JP-A 2001-194776 |
| JP-A 2001-296659 | JP-A 2002-226470 | JP-A 2002-249478 |
| JP-A 2002-363146 | JP-A 2002-363148 | JP-A 2002-363152 |
| JP-A 2003-012621 | JP-A 2004-347735 | JP-A 2004-347736 |
| JP-A 2004-347738 | JP-A 2005-132749 | JP-A 2005-165295 |
| JP-A 2005-306812 | JP-A 2006-176468 | JP-A 2007-108451 |
| JP-A 2008-107513 | JP-A 2010-164933 | |

Examples of the quencher used in the resist composition are given below, but not limited thereto. Suitable primary aliphatic amines include cetylamine and tetraethylenepentamine. Suitable secondary aliphatic amines include didecylamine and didodecylamine. Suitable tertiary aliphatic amines include trioctylamine, tridecylamine, tridodecylamine, and N,N-dicyclohexylmethylamine.

Examples of suitable aromatic and heterocyclic amines include aniline derivatives (e.g., N,N-bis(2-hydroxyethyl)aniline and 2,6-diisopropylaniline), pyrrole derivatives, oxazole derivatives, thiazole derivatives, imidazole derivatives (e.g., 4-methyl-2-phenylimidazole and 2,4,5-triphenylimidazole), benzimidazole derivatives (e.g., benzimidazole, 2-methylbenzimidazole and 2-phenylbenzimidazole), pyrazole derivatives, furazan derivatives, pyrroline derivatives, pyrrolidine derivatives, imidazoline derivatives, imidazolidine derivatives, pyridine derivatives (e.g., dimethylaminopyridine and 2,6-di-t-butyl-4-methylpyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives, isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid derivatives (e.g., 4-dimethylaminobenzoic acid and 4-dibutylaminobenzoic acid) and amino acid derivatives. Examples of suitable nitrogen-containing compounds having hydroxyl group include triethanolamine, triisopropanolamine, 4-(2-hydroxyethyl)morpholine, and 3-quinuclidinol. Suitable N-oxides include tributylamine-N-oxide, N-methylmorpholine-N-oxide, and tris(2-methoxymethoxyethyl)amine-N-oxide. Suitable amide derivatives include 1-cyclohexylpyrrolidone and N-pivaloyl-2-phenylbenzimidazole. A typical imide derivative is phthalimide. Suitable carbamate derivatives include N-t-butoxycarbonyl-N,N-dicyclohexylamine, N-t-butoxycarbonylbenzimidazole, N-t-butoxycarbonyl-2-phenylbenzimidazole, N-benzyloxycarbonyl-2-phenylbenzimidazole and N-allyloxycarbonyl-2-phenylbenzimidazole.

Examples of suitable ammonium salts include triethylammonium camphorsulfonate, tetrabutylammonium acetate, tetrabutylammonium p-toluenesulfonate, tetrabutylammonium 2,4,6-triisopropylbenzenesulfonate, tetrabutylammonium camphorsulfonate, benzyltrimethylammonium camphorsulfonate, trimethyloctadecylammonium 2,4,6-triisopropylbenzenesulfonate, and 4-(2-cyclohexanecarboxyethyl)morpholinium camphorsulfonate.

Also included are tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris(2-acetoxyethyl)amine, tris(2-propionyloxyethyl)amine, tris(2-benzoyloxyethyl)amine, N,N-bis(2-acetoxyethyl)-2-(methoxycarbonyl)ethylamine, N,N-bis(2-methoxyethyl)-2-(methoxycarbonyl)ethylamine, 1-[2-(methoxymethoxy)ethyl]-2-phenylbenzimidazole, 1-dodecylpiperidine, 1-[2-[(2-methoxyethoxy)methoxy]ethyl]pyrrolidine, 4-dodecylmorpholine, 1-[2-[(2-methoxyethoxy)methoxy]ethyl]piperidine, 4-[2-[(2-methoxyethoxy)methoxy]ethyl]morpholine, 4-[2-[2-(2-methoxyethoxy)ethoxy]ethyl]morpholine, 1-[2-[2-(2-methoxyethoxy)ethoxy]ethyl]benzimidazole, 4-[2-[2-[2-(2-methoxyethoxy)ethoxy]ethoxy]ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazolyl)ethyl acetate, 2-(2-phenyl-1-benzimidazolyl)ethyl acetate, 2-piperidinoethyl 2-(2-methoxyethoxy)acetate, 2-morpholinoethyl 2-(2-methoxyethoxy)acetate, 2-(1-benzimidazolyl)ethyl 2-(2-methoxyethoxy)acetate, 2-(2-phenyl-1-benzimidazolyl)ethyl 2-(2-methoxyethoxy)acetate, 2-(1- pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-benzimidazolyl)ethyl 2-[2-(2-methoxyethoxy)ethoxy] acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris (O-acetyl)cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-morpholinoethyl 2-naphthalenecarboxylate, and 2-morpholinoethyl 7-oxanorbornane-2-carboxylate.

An appropriate amount of the quencher is 0.01 to 20 parts, and more preferably 0.1 to 10 parts by weight per 100 parts by weight of the overall base resin. Less than 0.01 part of the quencher may be ineffective whereas more than 20 parts may adversely affect sensitivity.

Optionally, a surfactant (F) may be added to the resist composition. The surfactant used herein is not particularly limited, and may be selected from a wide range of well-known compounds. Reference may be made to US 20090274978 (JP-A 2009-269953, paragraphs [0142]-[0149]). The surfactants which can be added to resist compositions are generally divided into two groups: surfactants (F1) which are commonly used for facilitating coating operation and surfactants (F2) which are added in the immersion lithography using water in the absence of a resist protective film.

Preferred examples of surfactant (F1) include FC-4430 (3M-Sumitomo Co., Ltd.), and Surflon S-381, Surfynol E1004, KH-20 and KH-30 (all available from AGC Seimi Chemical Co., Ltd.), and partially fluorinated oxetane ring-opening polymerization polymers. These surfactants may be used alone or in admixture. The surfactant (F1) is preferably added in an amount of up to 2 parts, more preferably up to 1 part by weight per 100 parts by weight of the base resin.

When formulated in resist material, the surfactant (F2) segregates at the surface of a resist film as spin coated and functions to prevent or mitigate penetration of water into the resist film and leaching of resist components from the resist film during exposure under water immersion conditions. A surfactant (F2) may be selected from a variety of well-known compounds as long as they have the desired function. They are typically polymeric surfactants which do not dissolve in water, but in alkaline developer and exhibit high water repellency and improved water slip.

Preferred examples of surfactant (F2) include those described in JP-A 2007-297590, JP-A 2008-122932, JP-A 2009-098638, JP-A 2009-191151, JP-A 2009-192784, JP-A 2009-276363, JP-A 2010-107695, and JP-A 2010-134012.

When added to the resist composition, surfactant (F2) is preferably used in an amount of 0.001 to 20 parts, more preferably 0.01 to 10 parts by weight per 100 parts by weight of the base resin. Reference may be made to JP-A 2007-297590.

If desired, other additives may be added to the resist composition, for example, dissolution regulators, acetylene alcohols, acidic compounds, dyes, thermal crosslinkers, and stabilizers. Suitable dissolution regulators and acetylene alcohols are described in JP-A 2008-122932, paragraphs [0155]-[0178] and [0179]-[0182], respectively.

Using the resist composition of the invention, patterns may be formed by any known lithographic technique. Typically, the composition is applied onto a substrate for IC microfabrication (e.g., Si, $SiO_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 60 to 150° C. for about 0.1 to 10 minutes, preferably 80 to 140° C. for 0.5 to 5 minutes. The resulting resist film is generally 0.05 to 2.0 μm thick. A mask having the desired pattern is placed over the resist film, and the resist film is then exposed to radiation, preferably having an exposure wavelength of up to 300 nm, such as UV, deep-UV, EUV, excimer laser light, EB, x-ray, γ-ray and synchrotron radiation. The exposure dose is preferably in the range of 1 to 200 mJ/cm$^2$, more preferably 10 to 100 mJ/cm$^2$. Light exposure may be done by a conventional exposure process or in some cases, by an immersion lithography process of providing a liquid fill, typically water, between the projection lens and the resist film. In the case of immersion lithography, if necessary, a topcoat may be applied onto the resist film before exposure, which is generally know as "top coat process." The resist film is then baked (PEB) on a hot plate at 60 to 150° C. for 0.1 to 5 minutes, and preferably at 80 to 140° C. for 0.5 to 3 minutes. Finally, development may be carried out using as the developer an aqueous alkali solution, such as 0.1 to 5 wt %, and preferably 2 to 3 wt %, tetramethylammonium hydroxide (TMAH), this being done by a conventional method such as dip, puddle, or spray technique for a period of 0.1 to 3 minutes, and preferably 0.5 to 2 minutes. These steps result in the formation of the desired pattern on the substrate. If necessary, the pattern as developed can be heat treated or chemically shrunk for adjusting the pattern size, the heat treatment being generally known as "thermal flow" process. Of the various types of high-energy radiation that may be used, the resist composition of the invention is best suited to micro-pattern formation with, in particular, deep-UV having a wavelength of 260 to 120 nm or excimer laser, EUV, x-ray and EB.

EXAMPLE

Synthesis Examples, Examples and Comparative Examples are given below by way of illustration and not by way of limitation. Mw and Mn of a polymer are determined by GPC versus polystyrene standards using tetrahydrofuran as eluate. All parts are by weight (pbw). Me stands for methyl.

Synthesis Example

Acid-decomposable keto ester compounds of steroid skeleton were synthesized by the following method.

Synthesis Example 1

Synthesis of 1-ethylcyclopentyloxycarbonylmethyl dehydrocholate (A-1)

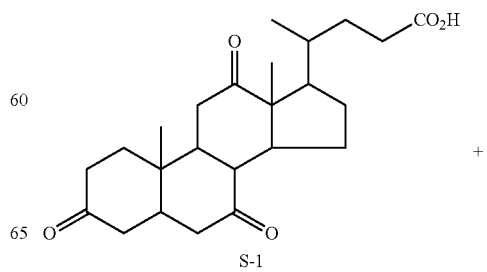

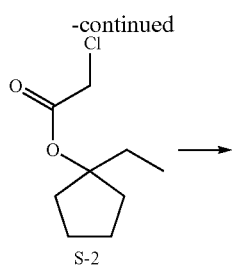

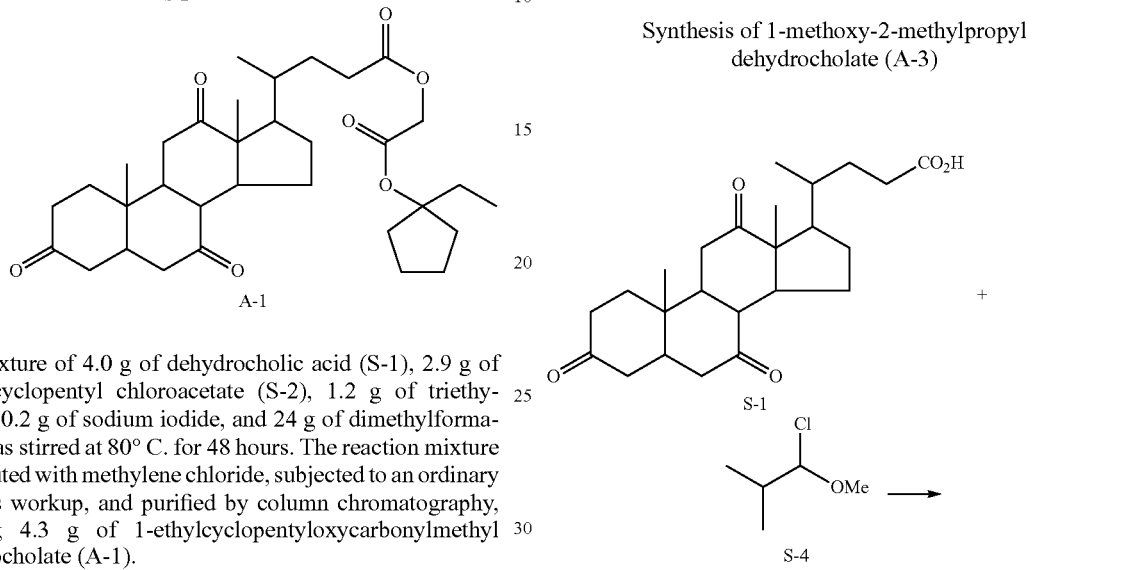

A mixture of 4.0 g of dehydrocholic acid (S-1), 2.9 g of 1-ethylcyclopentyl chloroacetate (S-2), 1.2 g of triethylamine, 0.2 g of sodium iodide, and 24 g of dimethylformamide was stirred at 80° C. for 48 hours. The reaction mixture was diluted with methylene chloride, subjected to an ordinary aqueous workup, and purified by column chromatography, yielding 4.3 g of 1-ethylcyclopentyloxycarbonylmethyl dehydrocholate (A-1).

Synthesis Example 2

Synthesis of 1-ethylcyclopentyl dehydrocholate (A-2)

A mixture of 4.2 g of dehydrocholic acid chloride (S-3), 1.7 g of 1-ethylcyclopentanol (S-4), 0.1 g of 4-dimethylaminopyridine, and 16 g of pyridine was stirred at 60° C. for 16 hours. The reaction mixture was diluted with methylene chloride, subjected to an ordinary aqueous workup, and purified by column chromatography, yielding 3.5 g of 1-ethylcyclopentyl dehydrocholate (A-2).

Synthesis Example 3

Synthesis of 1-methoxy-2-methylpropyl dehydrocholate (A-3)

At room temperature, 6.1 g of 1-chloro-2-methylpropyl methyl ether (S-5) was added dropwise to a mixture of 20.0 g of dehydrocholic acid (S-1), 6.0 g of triethylamine, and 100 g of tetrahydrofuran, followed by stirring for 1 hour. The reaction mixture was diluted with toluene. After an ordinary aqueous workup, the solvent was distilled off in vacuum. The resulting solid was washed with isopropyl ether and dried in vacuum, yielding 21.9 g of 1-methoxy-2-methylpropyl dehydrocholate (A-3).

The target compound was analyzed by infrared (IR) absorption spectroscopy and nuclear magnetic resonance spectroscopy ($^1$H-NMR), with the results shown below. Note that the compound is a mixture of two diastereomers in a ratio of 1:1.

IR (D-ATR): ν=2964, 2931, 2872, 1740, 1720, 1705, 1470, 1426, 1384, 1314, 1299, 1277, 1250, 1220, 1170, 1138, 1120, 1097, 972, 946, 911 cm$^{-1}$ $^1$H-NMR (600 MHz, THF-d8):

δ=0.86 (3H, d, J=6.4 Hz), 0.88-0.92 (6H, m), 1.08 (3H, s), 1.22-1.42 (7H, m, inclusive of 1.40 (3H, s)), 1.55 (1H, dt, J=14.7, 4.1 Hz), 1.76-2.06 (9H, m), 2.09 (1H, dd, J=12.4, 5.5 Hz), 2.20 (1H, t, J=13.2 Hz), 2.23-2.52 (6H, m), 2.86 (1H, t, J=12.8 Hz), 2.96 (1H, dd, J=13.3, 5.5 Hz), 2.99 (1H, t, J=11.9 Hz), 3.32 (1.5H, s), 3.33 (1.5H, s), 5.52 (1H, d, J=5.0 Hz)

Synthesis Example 4

Synthesis of 2-methyl-1-(tricyclo[5.2.1.0$^{2,6}$]decan-8-yloxy)-propyl dehydrocholate (A-4)

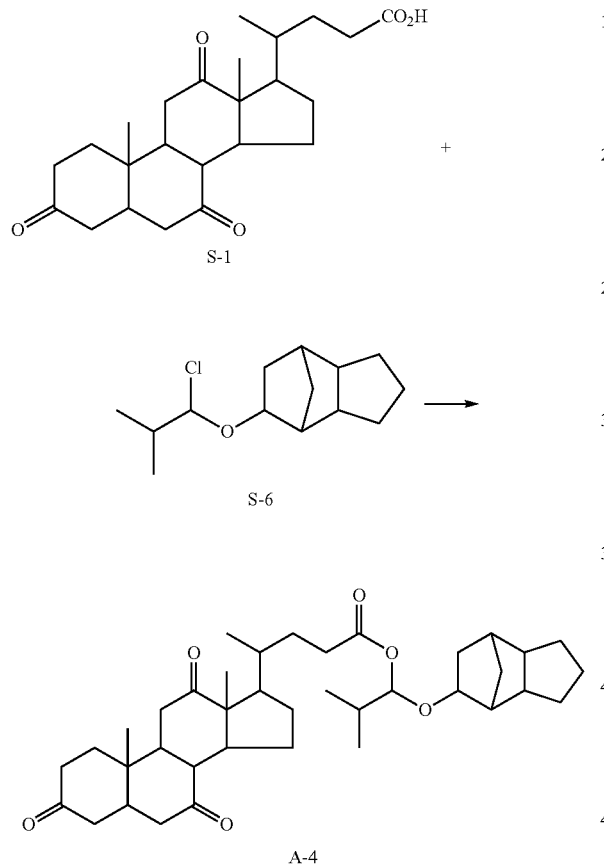

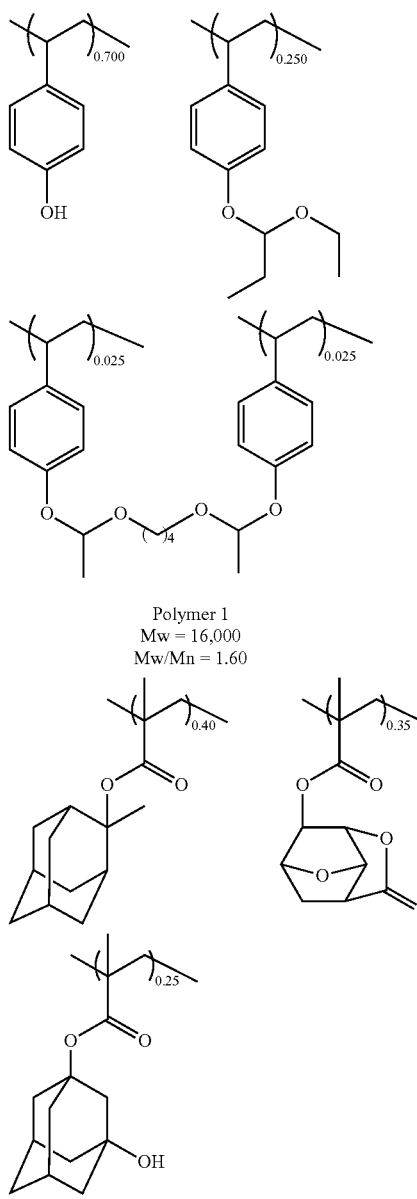

Synthesis was carried out as in Synthesis Example 3 aside from using an equimolar amount of 1-chloro-2-methylpropyl tricyclo[5.2.1.0$^{2,6}$]decan-8-yl ether (S-6) instead of 1-chloro-2-methylpropyl methyl ether (S-5). There was obtained 2-methyl-1-(tricyclo[5.2.1.0$^{2,6}$]decan-8-yloxy)propyl dehydrocholate (A-4).

Examples and Comparative Examples

Resist compositions were prepared using the acid-decomposable keto ester compounds synthesized above, and processed by the pattern forming process of the invention to form patterns which were evaluated for resolution and LER.

The base polymers, acid generators, quencher and acid-decomposable ester compounds used in Examples and Comparative Examples are identified below by their structural formulae.

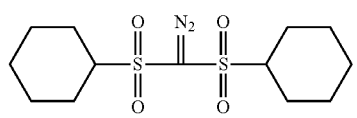

PAG 1

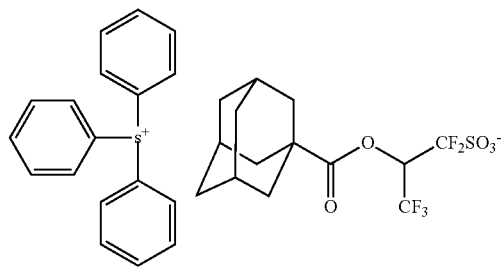

PAG 2

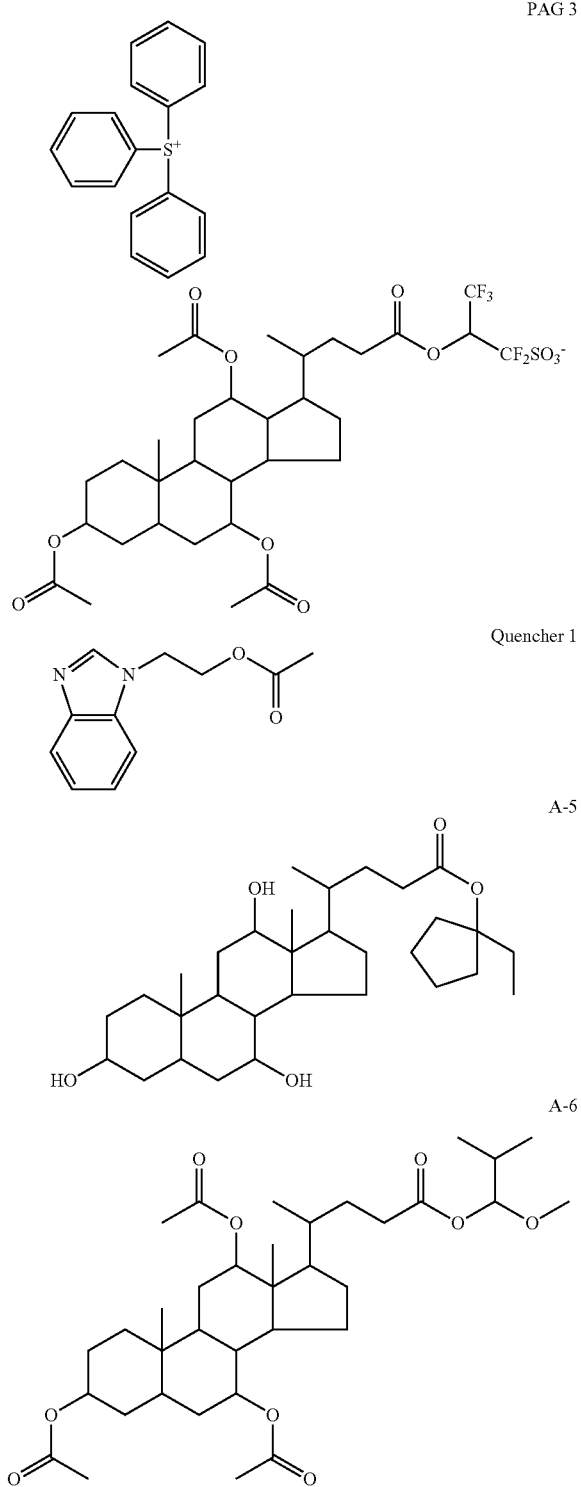

| Components | Parts |
|---|---|
| (A) Keto ester compound (A-1) | 6.0 |
| (B) Organic solvent: PGMEA | 400 |
| (C) Base resin: Polymer 1 | 100 |
| (D) Acid generator: PAG1 | 1.5 |
| PAG2 | 0.5 |
| (E) Quencher: Quencher 1 | 0.25 |
| (F) Surfactant: FC-4430 (3M-Sumitomo) | 0.01 |

Examples 2, 3 & Comparative Examples 1 to 3

Resist compositions were prepared as in Example 1 aside from using an equal amount of the acid-decomposable keto ester compound (A-2) or (A-3) in Synthesis Example 2 or 3, or comparative acid-decomposable ester compound (A-5) or (A-6). The resist composition of Comparative Example 1 was free of the acid-decomposable ester compound.

Tests of Examples and Comparative Examples

Resolution Test on KrF Lithography

Each resist composition was spin coated onto a silicon wafer having an antireflective coating of 55 nm thick (DUV30, Nissan Chemical Industries, Ltd.) and baked at 115° C. for 90 seconds to form a resist film of 550 nm thick. The resist film was exposed by means of a KrF excimer laser stepper NSR-S203B (Nikon Corp., NA=0.68, σ=0.75, ⅔ annular illumination), baked (PEB) at 110° C. for 90 seconds, cooled to 23° C., and puddle developed with a 2.38 wt % aqueous solution of tetramethylammonium hydroxide (TMAH) at 23° C. for 60 seconds, forming a 1:1 line-and-space pattern. The wafer as developed was observed under a top-down scanning electron microscope (TD-SEM). At the optimum exposure dose which provided a resolution of a 180-nm, 1:1 grouped line-and-space pattern, it was examined whether or not a 150-nm line-and-space pattern could be separated and resolved without peeling. The shape in cross section of the resolved resist pattern was examined under cross-sectional SEM and rated as an index of resolution (good for rectangular, and poor for footing and top loss). The LER of a 180-nm line-and-space pattern was observed and evaluated in three ratings of good, fair and poor. The test results (maximum resolution and LER) of inventive and comparative resist compositions are tabulated in Table 1.

TABLE 1

| | Acid-decomposable ester compound | 150 nm resolution | Pattern profile | LER |
|---|---|---|---|---|
| Example 1 | A-1 | resolved | rectangular: good | good |
| Example 2 | A-2 | resolved | rectangular: good | good |
| Example 3 | A-3 | resolved | rectangular: good | good |
| Comparative Example 1 | — | not completely separated | noticeable footing: poor | poor |
| Comparative Example 2 | A-5 | resolved | footing, top loss: poor | poor |
| Comparative Example 3 | A-6 | resolved | footing, top loss: poor | fair |

Example 1

A resist composition in solution form was prepared by combining the acid-decomposable keto ester compound (A-1) in Synthesis Example 1 with components in accordance with the following recipe, and filtering through a Teflon® filter with a pore size of 0.2 μm.

Example 4

A resist composition in solution form was prepared by combining the acid-decomposable keto ester compound (A-1) in Synthesis Example 1 with components in accordance with the following recipe, and filtering through a Teflon® filter with a pore size of 0.2 µm.

| Components | Parts |
|---|---|
| (A) Keto ester compound (A-1) | 7.5 |
| (B) Organic solvent: PGMEA | 800 |
| (C) Base resin: Polymer 2 | 100 |
| (D) Acid generator: PAG2 | 2.5 |
| (E) Quencher: Quencher 1 | 0.25 |
| (F) Surfactant: FC-4430 (3M-Sumitomo) | 0.01 |

Examples 5, 6 & Comparative Examples 4 to 6

Resist compositions were prepared as in Example 4 aside from using an equal amount of the acid-decomposable keto ester compound (A-2) or (A-3) in Synthesis Example 2 or 3, or comparative acid-decomposable ester compound (A-5) or (A-6). The resist composition of Comparative Example 4 was free of the acid-decomposable ester compound.

Tests of Examples and Comparative Examples

Resolution and LER Test on ArF Lithography

Each resist composition was spin coated onto a silicon wafer having an antireflective coating of 78 nm thick (ARC29A, Nissan Chemical Industries, Ltd.) and baked at 100° C. for 60 seconds to form a resist film of 100 nm thick. The resist film was exposed by means of an ArF excimer laser stepper 307E (Nikon Corp., NA=0.85, σ=0.93/0.70, ¾ annular illumination, 6% halftone mask), baked (PEB) at 110° C. for 60 seconds, and puddle developed with a 2.38 wt % TMAH aqueous solution for 30 seconds, forming a 1:1 line-and-space pattern. The wafer as developed was observed under a TD-SEM. The exposure dose which provides a 1:1 resolution of a 90-nm line-and-space pattern is an optimum dose. The maximum resolution is the minimum line width (on-mask size, in increments of 5 nm) of a line-and-space pattern which is separated and resolved at the optimum dose, with smaller values indicating better resolution. Using a measuring SEM S-9380 (Hitachi, Ltd.), the LER of a 90-nm line-and-space pattern was observed and evaluated in three ratings of good, fair and poor. The test results (maximum resolution and LER) of inventive and comparative resist compositions are tabulated in Table 2.

TABLE 2

| | Acid-decomposable ester compound | Maximum resolution | LER |
|---|---|---|---|
| Example 4 | A-1 | 75 nm | good |
| Example 5 | A-2 | 70 nm | good |
| Example 6 | A-3 | 65 nm | good |
| Comparative Example 4 | — | 80 nm | poor |
| Comparative Example 5 | A-5 | 80 nm | poor |
| Comparative Example 6 | A-6 | 80 nm | fair |

Example 7 & Comparative Example 7

A resist composition in solution form was prepared by combining the acid-decomposable keto ester compound (A-4) in Synthesis Example 4 with components in accordance with the following recipe, and filtering through a Teflon® filter with a pore size of 0.2 µm.

| Components | Parts |
|---|---|
| (A) Keto ester compound (A-4) | 100 |
| (B) Organic solvent: PGMEA | 3000 |
| (D) Acid generator: PAG3 | 5.0 |
| (E) Quencher: Quencher 1 | 0.25 |
| (F) Surfactant: FC-4430 (3M-Sumitomo) | 0.01 |

In Comparative Example 7, a resist composition was prepared as above aside from using Polymer 1 instead of the keto ester compound.

EB Writing Test

Using a coater/developer system Clean Track Mark 5 (Tokyo Electron Ltd.), the positive resist composition was spin coated onto a silicon substrate (diameter 6 inches, vapor primed with hexamethyldisilazane (HMDS) at 90° C.) and pre-baked on a hot plate at 110° C. for 60 seconds to form a resist film of 60 nm thick. Using a system HL-800D (Hitachi Ltd.) at a HV voltage of 50 keV, the resist film was exposed imagewise to EB in a vacuum chamber.

Using Clean Track Mark 5, immediately after the imagewise exposure, the wafer was baked (PEB) on a hot plate at 70° C. for 60 seconds and puddle developed in a 2.38 wt % TMAH aqueous solution for 30 seconds to form a positive pattern.

Resolution is a minimum size at the exposure dose that provides a 1:1 resolution of a 120-nm line-and-space pattern. The 120-nm line-and-space pattern was measured for LWR under SEM. The EB test results (maximum resolution and LER) of inventive and comparative resist compositions are tabulated in Table 3.

TABLE 3

| | Acid-decomposable ester compound | Maximum resolution | LER (nm) |
|---|---|---|---|
| Example 7 | A-4 | 70 nm | 3.5 |
| Comparative Example 7 | — | 80 nm | 8.0 |

It has been demonstrated that the resist composition of the invention meets both the requirements of high resolution and improved LER and is best suited for the photolithography of microfabrication. In particular, the acid-decomposable keto ester compound of steroid skeleton exerts an excellent effect when compounded in resist compositions.

Japanese Patent Application No. 2011-017812 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified positive resist composition comprising at least one acid-decomposable keto ester compound of steroid skeleton which is insoluble in alkaline developer, but turns soluble in alkaline developer under the action of acid, represented by the general formula (1):

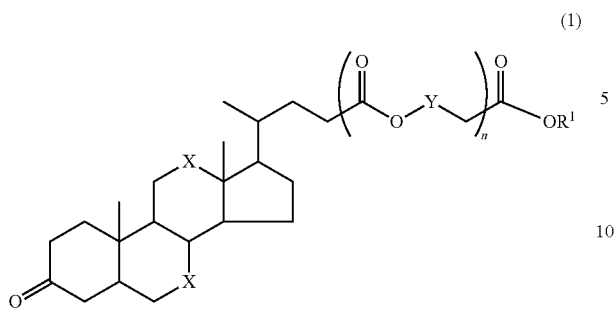

(1)

wherein $R^1$ is such an acid labile group having 6 to 20 carbon and oxygen atoms in total that —COOR$^1$ is decomposed to generate carboxyl under the action of acid, X is each independently a carbonyl group (—CO—) or methylene group (—CH$_2$—), Y is each independently a single bond or a $C_1$-$C_6$ alkylene group, and n is an integer of 0 to 2.

2. A chemically amplified positive resist composition comprising (A) at least one acid-decomposable keto ester compound of steroid skeleton which is insoluble in alkaline developer, but turns soluble in alkaline developer under the action of acid, represented by the general formula (1):

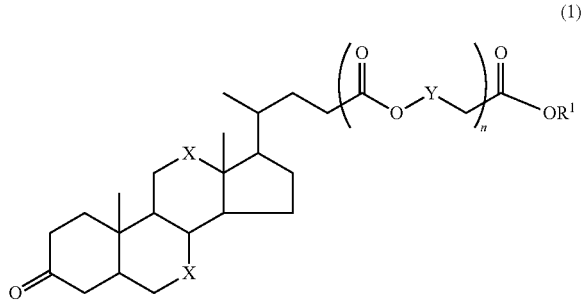

(1)

wherein $R^1$ is such an acid labile group having 6 to 20 carbon and oxygen atoms in total that —COOR$^1$ is decomposed to generate carboxyl under the action of acid, X is each independently a carbonyl group (—CO—) or methylene group (—CH$_2$—), Y is each independently a single bond or a $C_1$-$C_6$ alkylene group, and n is an integer of 0 to 2, (B) an organic solvent, (C) a base resin having an acidic functional group protected with an acid labile group, which is substantially insoluble in alkaline developer, but turns soluble in alkaline developer when the acid labile group is decomposed, and (D) an acid generator.

3. The resist composition of claim 2, further comprising (E) a quencher and/or (F) a surfactant.

4. The resist composition of claim 1 wherein the acid-decomposable keto ester compound has the general formula (2):

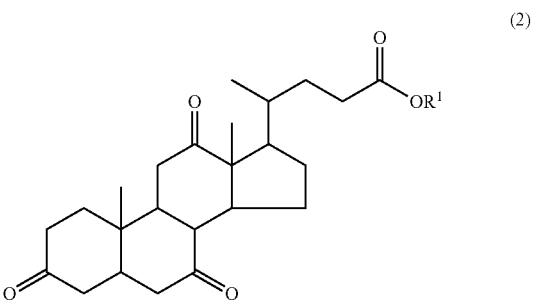

(2)

wherein $R^1$ is such an acid labile group having 6 to 20 carbon and oxygen atoms in total that —COOR$^1$ is decomposed to generate carboxyl under the action of acid.

5. The resist composition of claim 4 wherein the acid-decomposable keto ester compound has the general formula (3):

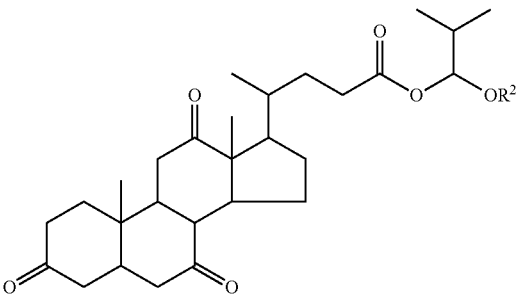

(3)

wherein $R^2$ is a straight, branched or cyclic alkyl group which may contain an oxygen atom and in which the sum of carbon and oxygen atoms is 1 to 15.

6. A pattern forming process comprising the steps of:
(i) coating the resist composition of claim 1 onto a substrate and prebaking to form a resist film,
(ii) exposing the resist film to high-energy radiation having a wavelength of up to 300 nm or electron beam through a photomask, and
(iii) baking and developing with a developer to form a resist pattern.

7. An acid-decomposable keto ester compound of steroid skeleton which is insoluble in alkaline developer, but turns soluble in alkaline developer under the action of acid, represented by the general formula (3):

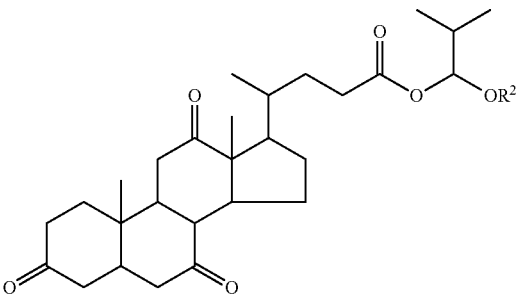

(3)

wherein $R^2$ is a straight, branched or cyclic alkyl group which may contain an oxygen atom and in which the sum of carbon and oxygen atoms is 1 to 15.

* * * * *